(12) United States Patent
Yoo et al.

(10) Patent No.: US 10,159,468 B2
(45) Date of Patent: Dec. 25, 2018

(54) ULTRASOUND DIAGNOSTIC APPARATUS AND METHOD AND COMPUTER READABLE STORAGE MEDIUM

(71) Applicant: SAMSUNG MEDISON CO., LTD., Hongcheon-gun (KR)

(72) Inventors: Jun-sang Yoo, Hongcheon-gun (KR); Sung-yoon Kim, Hongcheon-gun (KR); Kwang-hee Lee, Hongcheon-gun (KR); Jae-moon Jo, Seongnam-si (KR)

(73) Assignee: SAMSUNG MEDISON CO., LTD., Hongcheon-gun (KR)

( * ) Notice: Subject to any disclaimer, the term of this patent is extended or adjusted under 35 U.S.C. 154(b) by 203 days.

(21) Appl. No.: 14/669,392

(22) Filed: Mar. 26, 2015

(65) Prior Publication Data
US 2016/0051232 A1    Feb. 25, 2016

(30) Foreign Application Priority Data

Aug. 25, 2014  (KR) .......................... 10-2014-0111040

(51) Int. Cl.
*A61B 8/14* (2006.01)
*A61B 8/08* (2006.01)
(Continued)

(52) U.S. Cl.
CPC ............ *A61B 8/5223* (2013.01); *A61B 8/145* (2013.01); *A61B 8/468* (2013.01); *A61B 8/0808* (2013.01);
(Continued)

(58) Field of Classification Search
CPC ....... A61B 8/5223; A61B 8/468; A61B 8/145; A61B 8/523; A61B 8/0808; A61B 8/0866;
(Continued)

(56) References Cited

U.S. PATENT DOCUMENTS 6,149,594 A    11/2000  Rock et al.
6,458,081 B1 *  10/2002  Matsui .................... A61B 8/08
                                                                600/437
(Continued)

FOREIGN PATENT DOCUMENTS

EP        2612596 A1      7/2013
KR   10-2011-0059923 A    6/2011

OTHER PUBLICATIONS

Communication dated Mar. 11, 2015, issued by the European Patent Office in counterpart European Application No. 14199607.4.

Primary Examiner — Sanjay Cattungal
(74) Attorney, Agent, or Firm — Sughrue Mion, PLLC

(57) ABSTRACT

A method of more easily determining a measurement object that may be provided from a standard view for a user who is a doctor to read an ultrasound image in an ultrasound diagnosis. A data acquisition unit acquires ultrasound data of a target object. An image processor generates an ultrasound image by using the ultrasound data, acquires a standard view based on the ultrasound image, acquires measurement information that is information regarding measurement objects measurable within the standard view based on the standard view, and acquires at least one of the measurement objects based on the acquired measurement information.

24 Claims, 21 Drawing Sheets

(51) Int. Cl.
*A61B 8/00* (2006.01)
*G01S 7/52* (2006.01)

(52) U.S. Cl.
CPC ............. *A61B 8/0866* (2013.01); *A61B 8/463* (2013.01); *A61B 8/467* (2013.01); *A61B 8/523* (2013.01); *A61B 8/5207* (2013.01); *A61B 8/565* (2013.01); *G01S 7/52073* (2013.01); *G01S 7/52074* (2013.01)

(58) Field of Classification Search
CPC ....... A61B 8/5207; A61B 8/467; A61B 8/565; A61B 8/463; G01S 7/52074; G01S 7/52073
USPC .................................................. 600/437–469
See application file for complete search history.

(56) References Cited

U.S. PATENT DOCUMENTS

| | | | |
|---|---|---|---|
| 9,289,186 B2 * | 3/2016 | Tashiro | A61B 8/44 |
| 2006/0270938 A1 | 11/2006 | Yawata | |
| 2010/0022877 A1 | 1/2010 | Chono | |
| 2012/0065512 A1 | 3/2012 | Hamada et al. | |
| 2013/0158402 A1 | 6/2013 | Annangi et al. | |
| 2013/0324850 A1 * | 12/2013 | Petruzzelli | A61B 8/467 |
| | | | 600/443 |
| 2014/0369583 A1 * | 12/2014 | Toji | A61B 8/06 |
| | | | 382/131 |

* cited by examiner

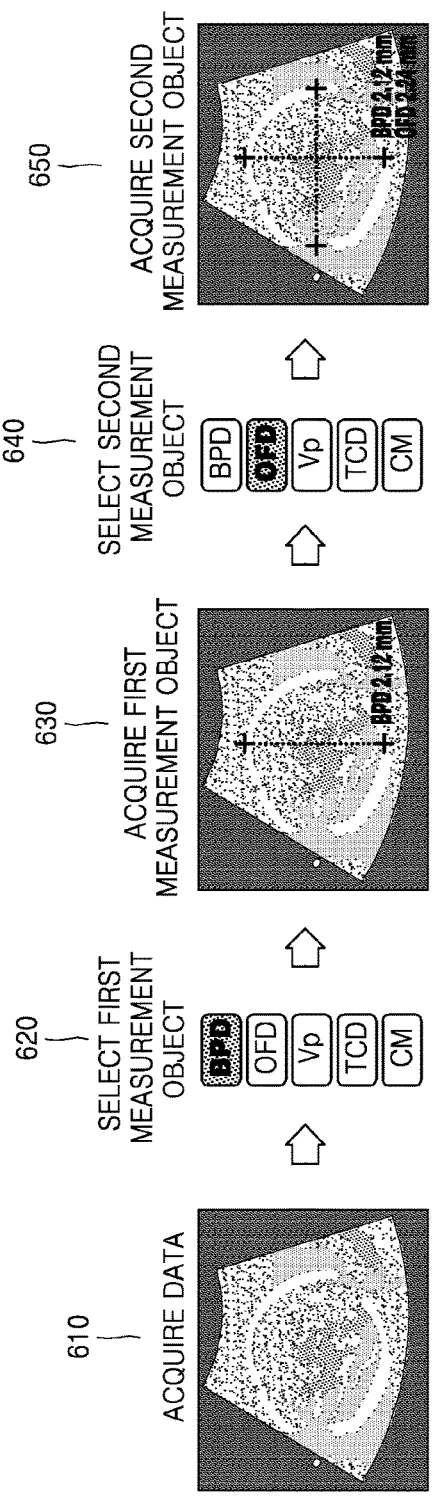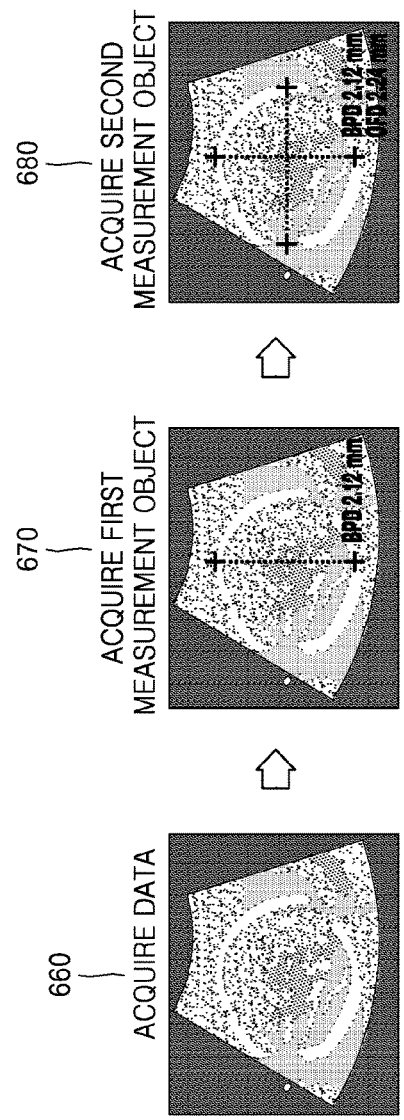
FIG. 6A
FIG. 6B

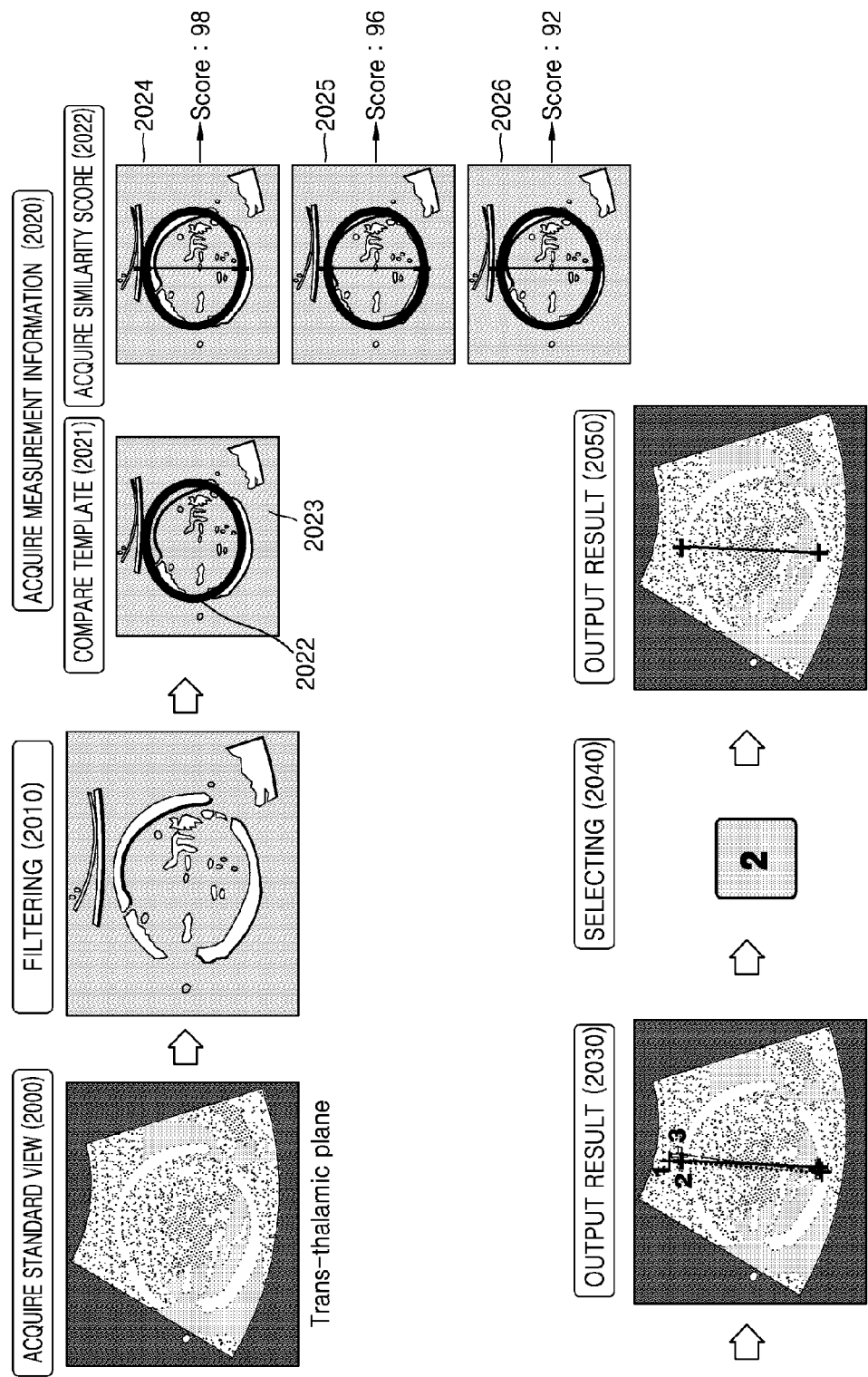

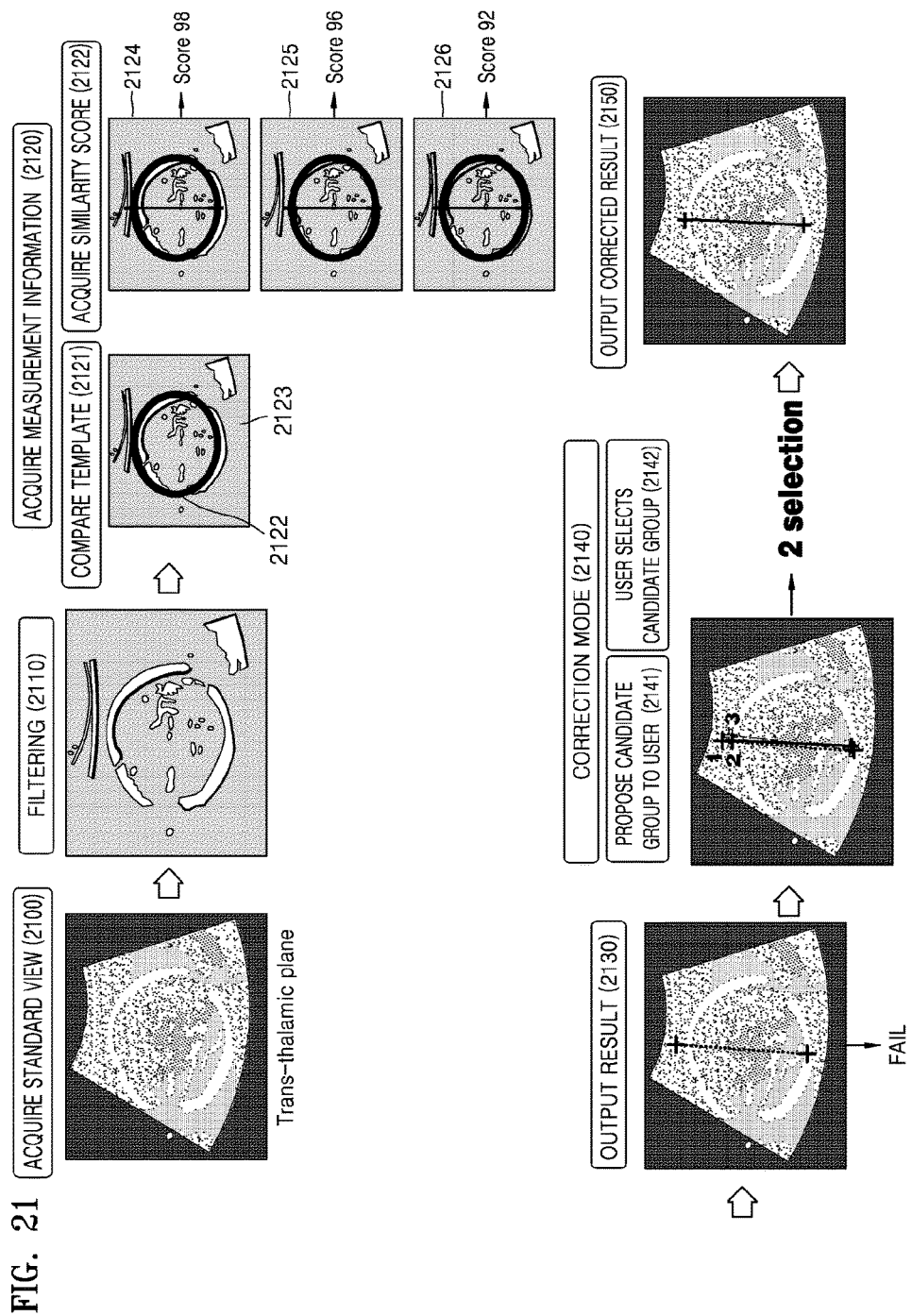

ULTRASOUND DIAGNOSTIC APPARATUS AND METHOD AND COMPUTER READABLE STORAGE MEDIUM

RELATED APPLICATIONS

This application claims the benefit of Korean Patent Application No. 10-2014-0111040, filed on Aug. 25, 2014, in the Korean Intellectual Property Office, the disclosure of which is incorporated herein in its entirety by reference.

BACKGROUND

1. Field

One or more embodiments of the present invention relate to an ultrasound diagnosis apparatus and a method of imaging an ultrasound image, and more particularly, to an ultrasound diagnosis apparatus for acquiring measurement objects that are measurable from a standard view of an ultrasound image and a method of imaging the ultrasound image.

2. Description of the Related Art

An ultrasound diagnosis apparatus irradiates an ultrasound signal generated by a transducer of a probe to a target object, and receives information about an echo signal reflected from the target object to obtain an image of a region inside the target object. In detail, the ultrasound diagnosis apparatus is used for medical purposes, for example, to observe the inside of the target object, to detect a foreign substance, and to measure an injury. Such an ultrasound diagnosis apparatus is widely used together with another imaging diagnostic apparatus since the ultrasound diagnosis apparatus has high stability compared to a diagnostic apparatus using an X-ray, is capable of displaying an image in real-time, and is safe because of no radiation exposure.

In this connection, it is necessary to provide a method of more easily determining a measurement object that may be provided from a standard view to a user who is a doctor in reading an ultrasound image.

The user has searched for and measured standard views in a conventional ultrasound system. In this regard, each standard view has a plurality of measurement objects. To measure each measurement object, the user has selected an object that is to be measured on an ultrasound diagnosis apparatus, inputted measurement information, and measured the object, and thus there is an inconvenience that a plurality of user inputs is necessary for acquiring and measuring a single measurement object.

SUMMARY

One or more embodiments of the present invention include an ultrasound diagnosis apparatus and method for minimizing a user input and accurately acquiring and measuring a measurement object and a computer readable storage medium.

Additional aspects will be set forth in part in the description which follows and, in part, will be apparent from the description, or may be learned by practice of the presented embodiments.

According to one or more embodiments of the present invention, an ultrasound diagnosis apparatus includes a data acquisition unit for acquiring ultrasound data of a target object; and an image processor for generating an ultrasound image by using the ultrasound data, acquiring a standard view based on the ultrasound image, acquiring measurement information that is information regarding measurement objects measurable within the standard view, based on the standard view, and acquiring at least one of the measurement objects, based on the acquired measurement information.

The ultrasound diagnosis apparatus may further include: a user input unit for receiving user inputs on the acquired standard view.

The received user inputs may be point information on the standard view, and wherein the image processor acquires the measurement information based on the received user inputs.

The image processor may acquire the measurement objects by determining whether the measurement information is included in a range of predetermined measurement information corresponding to one of the measurement objects.

The image processor may extract shape information of the target object based on the standard view and acquire the measurement information based on the extracted shape information including an outline.

The ultrasound diagnosis apparatus may further include: an output unit for outputting at least one of the generated ultrasound image, the standard view, the measurement information, and the measurement objects as at least one of an image, sound, and computer readable data.

The image processor may automatically acquire measurable measurement information based on at least one of a type of the standard view, location information of the target object, and direction information of the target object.

The image processor may acquire a plurality of standard views and acquire the measurement objects corresponding to each of the plurality of standard views.

The ultrasound diagnosis apparatus may further include: a storage unit for storing a predetermined template of the measurement information according to a type of the standard view, wherein the image processor acquires one or more candidate groups regarding the measurement information, based on at least one of the predetermined template and the standard view.

The image processor may acquire scores of the one or more candidate groups according to a similarity between the predetermined template and the standard view.

The ultrasound diagnosis apparatus may further include: an output unit for outputting at least one of the one or more candidate groups and the acquired scores to a user.

The image processor may change at least one of the measurement information based on at least one of the received user inputs for changing the measurement objects and the acquired measurement information and acquires the measurement objects, based on the changed measurement information.

An indicator may correspond to the received user inputs, and the changed measurement information may be acquired based on a location of the indicator on the standard view and the acquired measurement information.

The image processor may acquire the measurement information and the measurement objects in real time according to the user inputs.

The ultrasound diagnosis apparatus may further include: a storage unit for storing a predetermined template of the measurement information according to a type of the standard view, wherein the image processor acquires one of more candidate groups with respect to the measurement information based on at least one of the received user inputs, the predetermined template, and the standard view.

The image processor may acquire scores of the one or more candidate groups according to a similarity between the predetermined template and the standard view.

The ultrasound diagnosis apparatus may further include: an output unit for outputting at least one of the one or more candidate groups and the acquired scores to a user.

The standard view may include at least one of Training, a Harr pattern, and Sobel detection.

The standard view may include at least one of a mid-sagittal plane, a transventricle plane, a transthalamic plane, a transcerebellar plane, a four-chamber view, a five chamber view, a three vessel view, an RVOT (Right Ventricular Outflow Tract), an LVOT (Left Ventricular Outflow Tract), a bicaval view, an aortic arch, a ductal arch, a high short axis view, a low short axis view.

The measurement information may include at least one of a direction of a caliper, a location, a type, and location information of points.

The measurement objects may include at least one of CRL (Crown-rump length), NT (Nuchal translucency), IT (Intracranial Translucency) related to fetus, HC (Head Circumference), BPD (Bi-parietal Diameter), OFD (Occipital Frontal Diameter), Vp (Posterior Cerebral Ventricle Diameter), TCD (Transverse Cerebellar Diameter), CM (Cisterna Magna) related to a brain, and femur, tibia, fibula, ulna, radius, and humerus related to a bone.

The image processor may include a filter for clearly displaying a characteristic of the standard view to extract the shape information of the target object.

According to one or more embodiments of the present invention, an ultrasound diagnosis method includes acquiring ultrasound data of a target object; generating an ultrasound image by using the ultrasound data, and acquiring a standard view, based on the ultrasound image; acquiring measurement information that is information regarding measurement objects measurable within the standard view, based on the standard view; and acquiring at least one of the measurement objects based on the acquired measurement information.

The ultrasound diagnosis method may further include: receiving user inputs on the acquired standard view; and acquiring the measurement information based on the received user inputs.

According to one or more embodiments of the present invention, there is provided a computer readable recording medium having embodied thereon a computer program for executing the method.

BRIEF DESCRIPTION OF THE DRAWINGS

These and/or other aspects will become apparent and more readily appreciated from the following description of the embodiments, taken in conjunction with the accompanying drawings in which:

FIGS. 6A and 6B are diagrams for comparing the related art and the present invention;

FIG. 20 illustrates ultrasound diagnosis screens for explaining a process of acquiring a measurement object according to an embodiment of the present invention;

FIG. 21 illustrates ultrasound diagnosis screens for explaining a process of acquiring a measurement object according to another embodiment of the present invention.

DETAILED DESCRIPTION

The terms used in this specification are those general terms currently widely used in the art in consideration of functions in regard to the present invention, but the terms may vary according to the intention of those of ordinary skill in the art, precedents, or new technology in the art. Also, specified terms may be selected by the applicant, and in this case, the detailed meaning thereof will be described in the detailed description of the invention. Thus, the terms used in the specification should be understood not as simple names but based on the meaning of the terms and the overall description of the invention.

Throughout the specification, it will also be understood that when a component "includes" an element, unless there is another opposite description thereto, it should be understood that the component does not exclude another element but may further include another element. In addition, terms such as " . . . unit", " . . . module", or the like refer to units that perform at least one function or operation, and the units may be implemented as hardware or software or as a combination of hardware and software.

Throughout the specification, an "ultrasound image" refers to an image of a target object obtained using an ultrasound wave. Furthermore, in the present specification, a "target object" may include a person or an animal, or a part of a person or an animal. For example, the target object may include the liver, the heart, the womb, the brain, a breast, the abdomen, or a blood vessel. Furthermore, the "target object" may include a phantom. A phantom is a material having a volume that is approximately the density and effective atomic number of a living thing, and may include a sphere phantom having a property similar to a human body.

Furthermore, in the present specification, "user" refers to a medical professional, such as a doctor, a nurse, a medical laboratory technologist, or an engineer who repairs a medical apparatus, but the user is not limited thereto. Expressions such as "at least one of," when preceding a list of elements, modify the entire list of elements and do not modify the individual elements of the list.

Embodiments of the invention now will be described more fully hereinafter with reference to the accompanying drawings, in which illustrative embodiments of the invention are shown.

Figure 1:
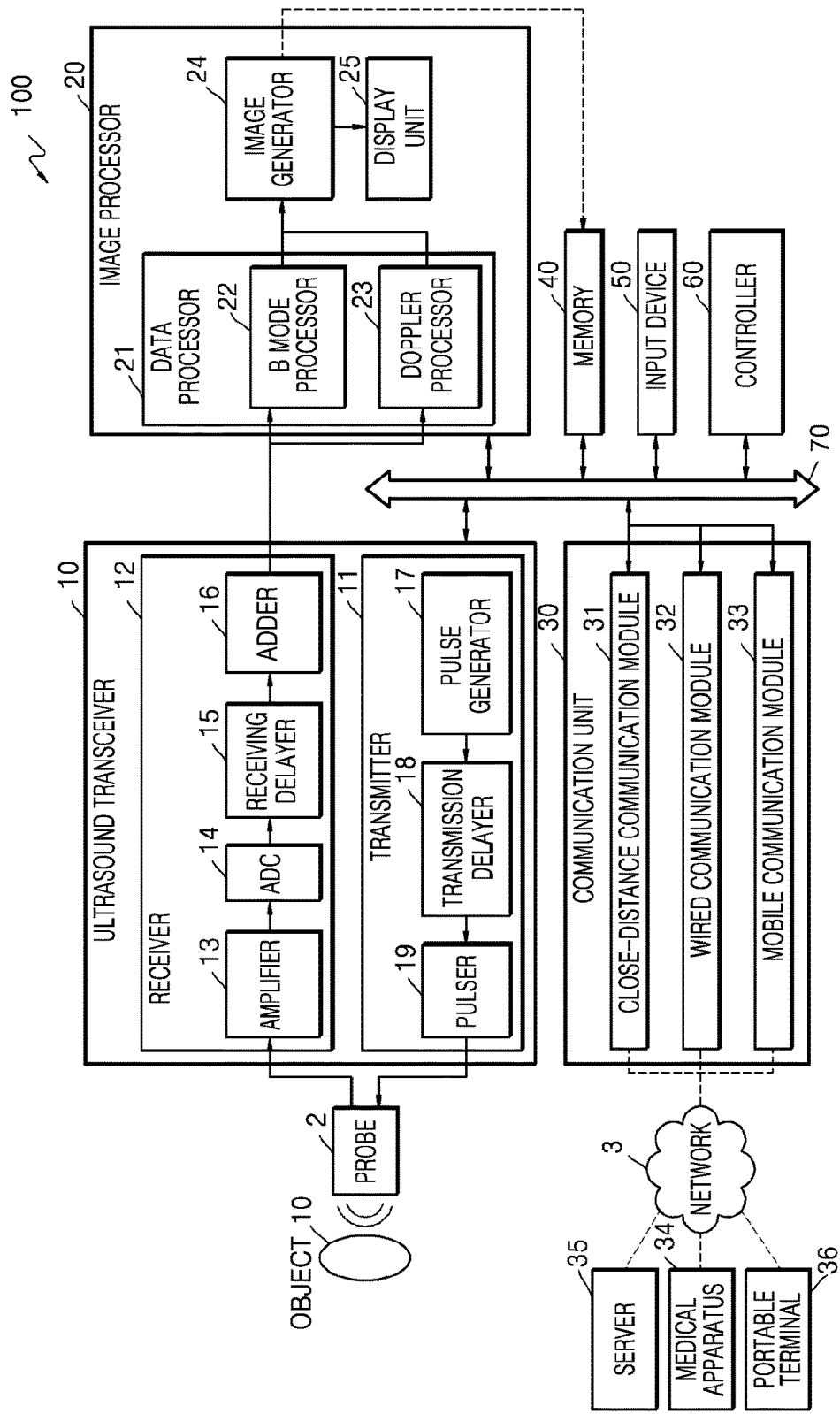
FIG. 1 is a block diagram of an ultrasound diagnosis apparatus according to an embodiment of the present invention.

FIG. 1 is a block diagram of an ultrasound diagnosis apparatus 100 according to an embodiment of the present invention.

Referring to FIG. 1, an entire construction of the ultrasound diagnosis apparatus 100 used in the present invention is illustrated.

The ultrasound diagnosis apparatus 100 may include a probe 2, an ultrasound transceiver 10, an image processor 20, a communication unit 30, a memory 40, an input device 50, and a controller 60, which may be connected to each other via a bus 70.

The ultrasound diagnosis apparatus 100 may be embodied not only as a cart type apparatus, but also as a portable apparatus. Examples of portable ultrasound diagnosis apparatuses may include a picture archiving and communications system (PACS) viewer, a smart phone, a laptop computer, a personal digital assistant (PDA), and a tablet PC, but are not limited thereto.

The probe 2 transmits an ultrasound signal to a target object 1 based on a driving signal applied by the ultrasound transceiver 10 and receives an echo signal reflected by the target object 1. The probe 2 includes a plurality of transducers that oscillate based on electric signals transmitted thereto and generate ultrasound waves, that is, acoustic energy. Furthermore, the probe 2 may be connected to a main body of the ultrasound diagnosis apparatus 100 via wires or wirelessly. According to embodiments of the present invention, the ultrasound diagnosis apparatus 100 may include a plurality of probes 2.

The transmitter 11 supplies a driving signal to the probe 2 and includes a pulse generator 17, a transmission delayer 18, and a pulser 19. The pulse generator 17 generates pulses for forming transmission ultrasound signals based on a predetermined pulse repetition frequency (PRF). The transmission delayer 18 applies a delay time to the pulses in order to determine transmission directionality of the ultrasound signal. Pulses to which the delay time is applied correspond to a plurality of vibrators included in the probe 2. The pulser 19 applies a driving signal (or a driving pulse) to the probe 2 at timing intervals corresponding to the pulses to which the delay time is applied.

The receiver 12 generates ultrasound data by processing echo signals received from the probe 2 and may include an amplifier 13, an analog-digital converter (ADC) 14, a reception delayer 15, and an adder 16. The amplifier 13 amplifies the echo signals in each channel. The ADC 14 analog-to-digital converts the amplified echo signals. The reception delayer 15 processes the digitally-converted echo signals by applying delay times for determining reception directionality to the digitally-converted echo signals. The adder 16 generates ultrasound data by adding the echo signals processed by the reception delayer 15. The receiver 12 may not include the amplifier 13 according to its embodiment. That is, the amplifier 13 may be omitted when a sensitivity of the probe 2 is improved or the number of processing bits of the ADC 14 increases.

The image processor 20 generates an ultrasound image by scan-converting ultrasound data generated by the ultrasound transceiver 10, and displays the ultrasound image. Meanwhile, an ultrasound image may include not only a grayscale ultrasound image obtained by scanning a target object in an A mode, a B mode, and a motion (M) mode, but also a Doppler image showing movement of the target object by using the Doppler effect. Examples of the Doppler image include a blood flow Doppler image showing flow of blood (i.e., a color Doppler image), a tissue Doppler image showing movement of tissues, and a spectral Doppler image showing the speed at which a target object moves as a waveform.

A B mode processor 22 extracts B mode components from ultrasound data and processes the B mode components. An image generator 24 may generate an ultrasound image in which signal intensities are represented as brightness based on the extracted B mode components.

Similarly, a Doppler processor 23 may extract Doppler components from the ultrasound data. The image generator 24 may generate a Doppler image indicating movement of a target object as colors or waveforms based on the extracted Doppler components.

The image generator 24 according to an embodiment may generate a 3D ultrasound image by performing volume rendering on volume data and may generate an elastic image in which deformation of the target object 10 according to pressure is visualized. Furthermore, the image generator 24 may represent various types of additional information on the ultrasound image by using text and graphics. Meanwhile, the ultrasound image may be stored in the memory 40.

A display unit 25 displays the generated ultrasound image. The display unit 25 may display not only an ultrasound image, but also various types of information processed by the ultrasound diagnosis apparatus 100 on a screen via a graphic user interface (GUI). Meanwhile, the ultrasound diagnosis apparatus 100 may include two or more display units 25 according to embodiments of the present invention.

The communication unit 30 connected to a network 3 via wires or wirelessly and communicates with an external device or a server. The communication unit 30 may exchange data with a hospital server or another medical device in a hospital that is connected with a picture archiving and communications system (PACS). Furthermore, the communication unit 30 may perform data communication according to the digital imaging and communications in medicine (DICOM) standard.

The communication unit 30 may transmit and receive data related to diagnosis of the target object 1, e.g., an ultrasound image, ultrasound data, and Doppler data of the target object, via the network 3 and may also transmit and receive medical images obtained via other medical devices, e.g., a CT image, a MR image, and an X-ray image. Furthermore, the communication unit 30 may receive information related to a diagnosis history or treatment schedule of a patient from a server and utilize the information to diagnose the target object 1. Furthermore, the communication unit 30 may perform data communication not only with a server or a medical device in a hospital, but also with a portable terminal of a doctor or a patient.

The communication unit 30 is connected to the network 3 via wires or wirelessly and may exchange data with a server 35, a medical device 34, or a portable terminal 36. The communication unit 30 may include one or more components that enable communication with external devices, e.g., a close-distance communication module 31, a wired communication module 32, and a mobile communication module 33.

The close-distance communication module 31 may refer to a module for close-distance communication within a predetermined distance. Examples of close-distance communication techniques according to an embodiment of the present invention may include wireless LAN, Wi-Fi, Bluetooth, Zigbee, Wi-Fi Direct (WFD), ultra wideband (UWB), infrared data association (IrDA), Bluetooth Low Energy (BLE), and near field communication (NFC), but are not limited thereto.

The wired communication module 32 refers to a module for communication using electric signals or optical signals. Examples of wired communication techniques according to an embodiment of the present invention may include a pair cable, a coaxial cable, an optical fiber cable, and an Ethernet cable.

The mobile communication module 33 transmits and receives wireless signals with at least one from among a station, an external terminal, and a server on a mobile communication network. In this regard, the wireless signals may include voice call signals, video call signals, or various types of data for transmission and reception of text/multimedia messages.

The memory 40 stores various types of data processed by the ultrasound diagnosis apparatus 100. For example, the memory 40 may store medical data related to diagnosis of a target object, such as ultrasound data and ultrasound image that are input or output, and may also store algorithms or programs to be executed in the ultrasound diagnosis apparatus 100.

The memory 40 may be embodied as any of various storage media, e.g., a flash memory, a hard disk drive, an EEPROM, etc. Furthermore, the ultrasound diagnosis apparatus 100 may utilize a web storage server or a cloud server that functions as the memory 40 online.

The user device 50 receives an input by the user to control the ultrasound diagnosis apparatus 100. The user device 50 may include hardware components, such as a keypad, a mouse, a touch pad, a track ball, and a jog switch, but is not limited thereto. The user device 50 may further include various components, such as an electrocardiogram measuring module, a respiration measuring module, a voice recognition sensor, a gesture recognition sensor, a fingerprint recognition sensor, an iris recognition sensor, a depth sensor, a distance sensor, etc.

The controller 60 may control overall operations of the ultrasound diagnosis apparatus 100. In other words, the controller 60 may control operations among the probe 2, the ultrasound transceiver 10, the image processor 20, the communication unit 30, the memory 40, and the user device 50 of FIG. 1.

All or some of the probe 2, the ultrasound transceiver 10, the image processor 20, the communication unit 30, the memory 40, the user device 50, and the controller 60 may be implemented as software modules. However, an embodiment of the present invention is not limited thereto, and some of the components stated above may be implemented as hardware modules. Furthermore, at least one of the second ultrasound transceiver 10, the image processor 20, and the communication unit 30 may be included in the controller 60. However, an embodiment of the present invention is not limited thereto.

To diagnose disease by using the ultrasound image, a marker for setting a diagnosis part or displaying a predetermined position in the ultrasound image including the target object 1 may be set.

In more detail, the marker may be set in a part requiring a detailed observation for the user to determine a disease diagnosis or an existence of a medical condition of the patient. The present invention provides an ultrasound diagnosis apparatus that changes and outputs an ultrasound image such that the above-described marker more accurately diagnoses a set part of the target object, and a method of displaying the ultrasound image.

Figure 2:
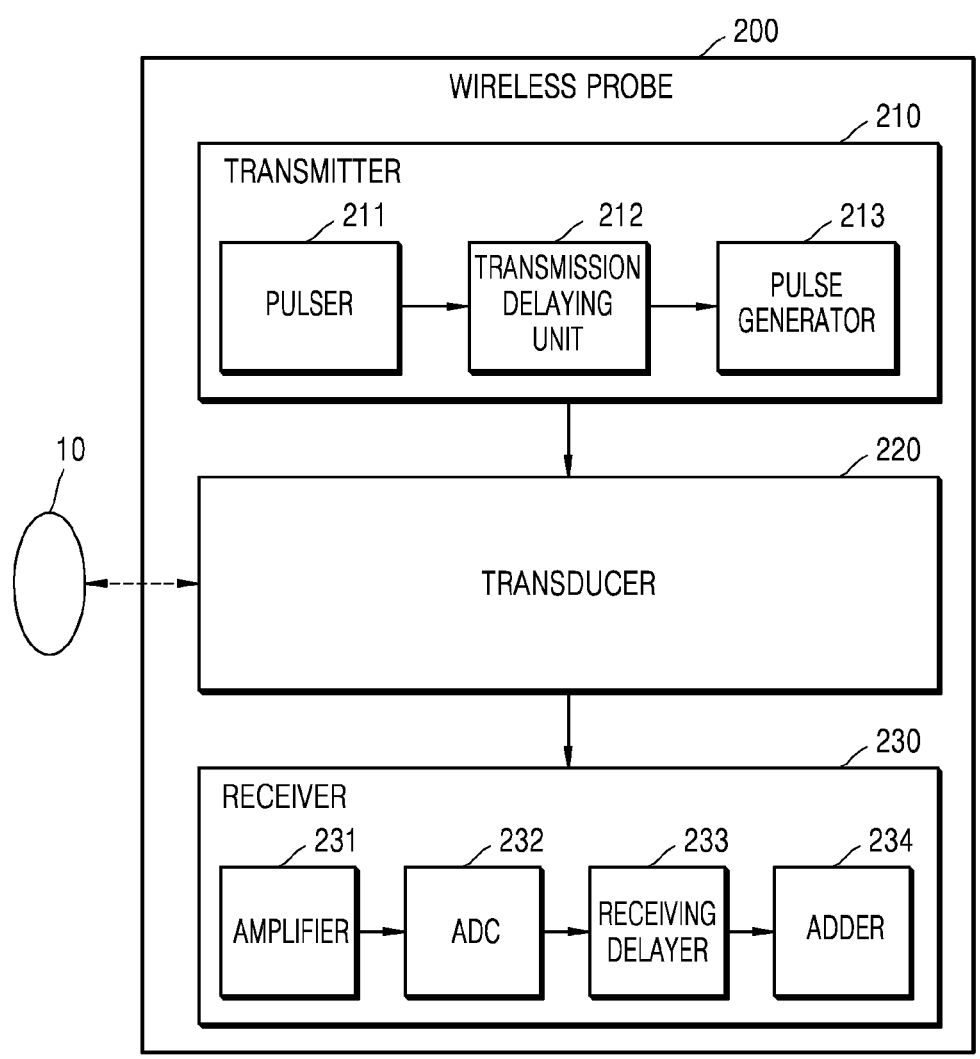
FIG. 2 is a block diagram of a wireless probe according to an embodiment of the present invention.

FIG. 2 is a block diagram of a wireless probe 200 according to an embodiment of the present invention.

The wireless probe 200 may include a plurality of transducers as described with reference to FIG. 1 above, and may include some or all of elements of the ultrasound transceiver 10 of FIG. 1 according to an embodiment.

The wireless probe 200 of FIG. 2 includes a transmitter 210, a transducer 220, and a receiver 230 that are described in detail with reference to FIG. 1 above, and thus detailed descriptions thereof are omitted. The wireless probe 200 may selectively include a reception delayer 233 and an adder 234 according to an embodiment.

The wireless probe 200 may transmit an ultrasound signal to the target object 1, receive an echo signal, generates ultrasound data, and wirelessly transmit the ultrasound data to the ultrasound diagnosis apparatus 100 of FIG. 1.

In a conventional ultrasound system, a user has searched for and measured standard views in a conventional ultrasound system. In this regard, each standard view has a plurality of measurement objects. To measure each measurement object, the user has selected an object that is to be measured on an ultrasound diagnosis apparatus, inputted measurement information, and measured the object.

Such a conventional technology has an inconvenience that a plurality of user inputs is necessary for acquiring a single measurement object.

According to an or another embodiment of the present invention, the user may accurately and conveniently acquire and measure a measurement object by overcoming the above-described problem of the conventional technology. An ultrasound diagnosis apparatus and method and a computer readable storage medium according to an or another embodiment of the present invention will be described in detail with reference to FIGS. 3 through 21 below.

Figure 3:
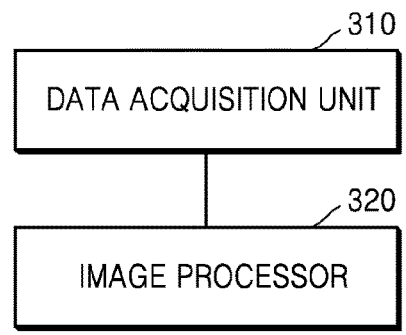
FIG. 3 is a block diagram of an ultrasound diagnosis apparatus according to an embodiment of the present invention.

FIG. 3 is a block diagram of an ultrasound diagnosis apparatus according to another embodiment of the present invention.

Referring to FIG. 3, the ultrasound diagnosis apparatus of the present invention includes a data acquisition unit 310 and an image processor 320. The data acquisition unit 310 performs ultrasonography on the target object 1 and acquires ultrasound data. The data acquisition unit 310 generates an ultrasound image by using the ultrasound data acquired from the data acquisition unit 310, acquires a standard view based on the ultrasound image, acquires measurement information that is information regarding measurement objects measurable in the standard view based on the standard view, and acquires at least one measurement objects based on the acquired measurement information.

The standard view is a view necessary for diagnosing a state or disease of the target object 1 in the ultrasound image. For example, when the target object 1 is a fetus, it is necessary to measure a crown rump length (CRL) that is a length from the crown of the fetus to the rump so as to observe a growth state according to a gestational age of the fetus. To measure the CRL, a mid-sagittal plane (MSP) that is a view indicating the CRL needs to be acquired. In the example described above, the standard view may be the MSP when measuring the CRL of the fetus. In this regard, the CRL may be a measurement object.

When a brain is observed by using the ultrasound diagnosis apparatus, the standard view may include the MSP, a transventricle plane, a transthalamic plane, a transcerebellar plane, etc. When a heart is observed by using the ultrasound diagnosis apparatus, the standard view may include a four-chamber view, a five chamber view, a three vessel view, a right ventricular outflow tract (RVOT), an left ventricular outflow tract (LVOT), a bicaval view, an aortic arch, a ductal arch, a high short axis view, a low short axis view, etc.

A method of acquiring the standard view may include at least one training, a Harr pattern, and a Sobel detection. Training is a method of searching for the standard view by repeating a process of detecting a pattern. The Harr pattern is a method of searching for the standard view by using a feature having a high similarity to that of a specific pattern among a plurality of Harr features. The Sobel detection is a method of searching for the standard view by detecting an outline on an image.

The measurement information that is information regarding measurement objects may include a caliper direction, a caliper location, a caliper type, and point location information. A caliper is a measurement point on a screen used to measure a thickness of a target object on an ultrasound image, a diameter, and a circumference. The caliper may include lines or points. The image processor 320 may automatically acquire measurement information measurable from a corresponding standard view based on at least one of a type of the standard view, location information of the target object 1, and direction information of the target object 1. For example, the image processor 320 performs image processing on the standard view such as outline improvement filtering and acquires the location information of the target object 1 and the direction information of the target object 1. The caliper may be automatically set to represent, for example, a major axis of the target object 1, a circumference, a minor axis, and a thickness. A direction of the set caliper, a location, a type, and location information of a point on the set caliper may be the measurement information.

The measurement object means an object that is to be measured to diagnose a disease of the target object 1, a state, whether the target object 1 is abnormal, etc. When the fetus is wholly observed, an object measurable in the standard view may include the CRL, a nuchal translucency (NT), and an intracranial translucency (IT). When the brain is observed, the object may include a head circumference (HC), a bi-parietal diameter (BPD), an occipital frontal diameter (OFD), a ventricle posterior (Vp), a trans cerebellum diameter (TCD), and a cisterna magna (CM). When a bone is observed, the object may include Femur, Tibia, Fibula, Ulna, Radius, and Humerus. The ultrasound diagnosis apparatus according to an embodiment of the present invention may acquire the measurement object based on the above-described measurement information.

Figure 17:
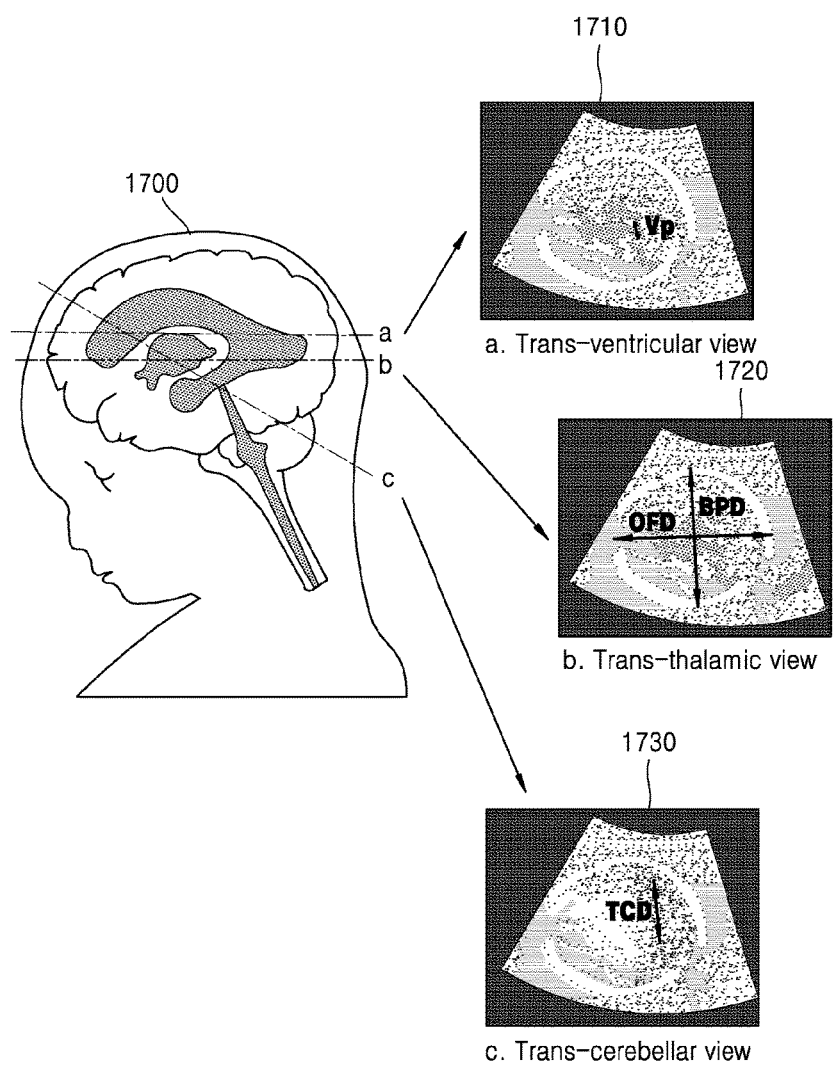
FIG. 17 is a diagram illustrating types of standard views with respect to a head of a fetus.

FIG. 17 illustrates types of standard views 1710, 1720, and 1730 with respect to a head 1700 of a fetus.

The standard view 1710 may be acquired by observing an axial section of the head 1700 of the fetus including a line a. A Vp may be most well observed in the standard view 1710, and thus the Vp may be a measurement object. The standard view 1720 may be acquired by observing an axial section of the head 1700 of the fetus including a line b. A BPD and an OFD may be most well observed in the standard view 1720, and thus the BPD or the OFD may be a measurement object. The standard view 1730 may be acquired by observing an axial section of the head 1700 of the fetus including a line c. A TCD may be most well observed in the standard view 1710, and thus the TCD may be a measurement object. That is, a measurement object that may be most well observed may be limited for each standard view.

Figure 19A:
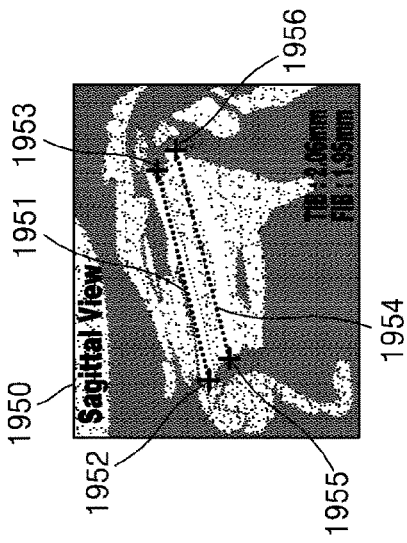
FIGS. 19A through 19C are diagrams of detailed examples of measurement objects according to types of standard views.
Figure 19B:
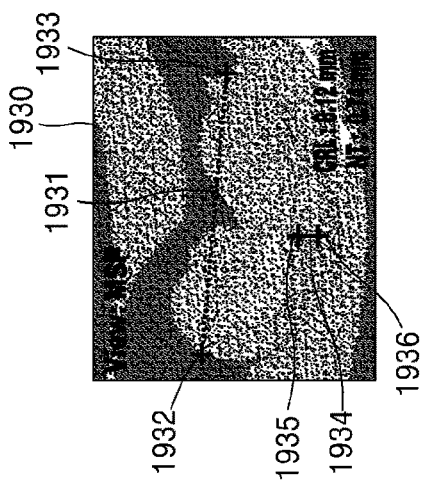
Figure 19C:
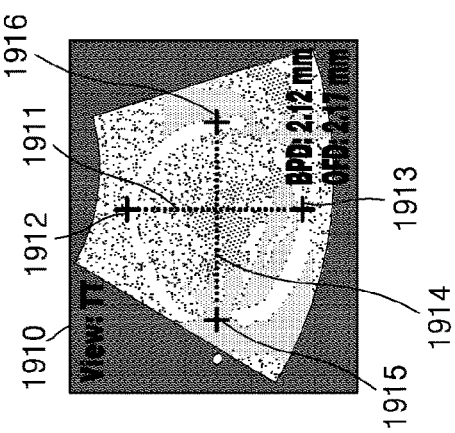

FIGS. 19A through 19C illustrate detailed examples of measurement objects according to types of standard views 1910, 1930, and 1950.

A TT standard view 1910 may be a standard view with respect to a head of a fetus. A BPD and an OFD may be included in measurement objects measurable in the TT standard view 1910. The measurement object BPD may be acquired according to information relating to a caliper 1911 that is measurement information. A measurement value acquired by the caliper 1911 may be 2.12 mm. The measurement object OFD may be acquired according to information relating to a caliper 1914 that is measurement information. That is, the measurement object may be determined based on at least one of a direction of the caliper 1914, a type, a location, and locations of points. The caliper 1914 may include points 1915 and 1916. A measurement value acquired by the caliper 1914 may be 2.47 mm.

A MSP standard view 1930 may be a standard view with respect to the fetus. Measurement objects that may be measured in the MSP standard view 1930 may include a CRL and an NT. The CRL means a length between the crown and the rump. The measurement object CRL may be acquired according to information relating to a caliper 1931 that is measurement information. The caliper 1931 for measuring the length may include points 1932 and 1933 at both ends of a predetermined length. For example, the point 1932 may be disposed in the crown. The point 1933 may be disposed in the rump. A measurement value of the CRL is a length between the points 1932 and 1933. A measurement value of the CRL acquired by the caliper 1931 may be 8.12 mm. A measurement object NT may be acquired according to information relating to a caliper 1934 that is measurement information. The caliper 1934 may include points 1935 and 1936. A measurement value of the NT acquired by the caliper 1934 may be 0.74 mm.

A sagittal view may be included along with the standard view 1950 regarding the bone of the fetus. Measurement objects that may be measured in the standard view 1950 may include TIB (Tibia) and FIB (Fibula). The measurement object FIB may be acquired according to information relating to a caliper 1951 that is measurement information. The caliper 1951 may include points 1952 and 1953. A measurement value of the FIB acquired by the caliper 1934 may be 1.95 mm. The measurement object TIB may be acquired according to information relating to a caliper 1954 that is measurement information. The caliper 1954 may include points 1955 and 1956. A measurement value of the TIB acquired by the caliper 1954 may be 2.06 mm.

Figure 4:
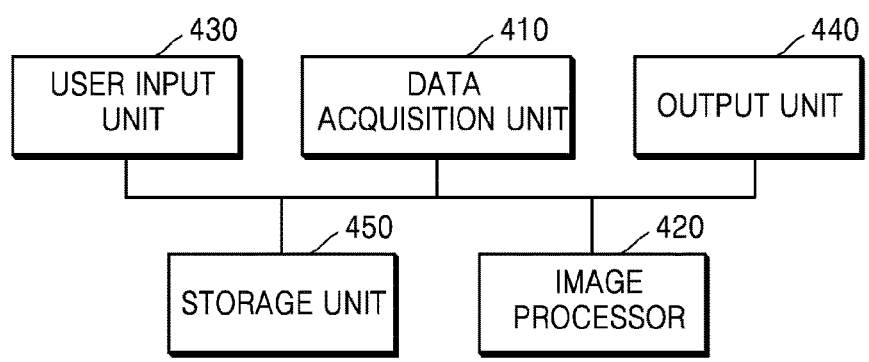
FIG. 4 is a detailed block diagram of an ultrasound diagnosis apparatus according to an embodiment of the present invention.

FIG. 4 is a detailed block diagram of the ultrasound diagnosis apparatus 100 according to another embodiment of the present invention. Referring to FIG. 4, a data acquisition unit 410 and an image processor 420 are respectively the same as the data acquisition unit 310 and the image processor 320 of FIG. 3, and thus detailed descriptions thereof are omitted.

The ultrasound diagnosis apparatus 100 may further include a user input unit 430, an output unit 440, and a storage unit 450, in addition to the data acquisition unit 410 and the image processor 420.

The user input unit 430 is a device that receives a user input. The user input unit 430 may use various devices that may receive the user input such as a mouse, a keyboard, a trackball, a touch pad, a touch display, etc. The user input by the user input unit 430 may display a mouse pointer, a cursor, etc. on a standard view as an indicator on a screen.

For example, the ultrasound diagnosis apparatus 100 may directly receive an user input with respect to the standard view through the user input unit 430. The user input received through the user input unit 430 may be point information on the standard view for acquiring measurement objects. The image processor 420 may acquire measurement information based on the received user input. For example, when the user inputs two points on the standard view, a caliper may be acquired based on the two points and a line connecting the two points. At least one of a direction of the acquired caliper, a type, a location, and locations of the points may be measurement information. The image processor 420 may newly acquire the measurement information based on at least one of the received user input and previously acquired measurement information from the user. A measurement object may be acquired based on the newly acquired measurement information. The ultrasound diagnosis apparatus 100 may receive the user input in real time, and the measurement information and the measurement object may be in real time acquired according to the user input. That is, the measurement information and the measurement object may be in real time acquired according to a movement of an indicator. For example, when the measurement information automatically acquired by the image processor 420 is inaccurate or inappropriate to measure the measurement object, the ultrasound diagnosis apparatus 100 may receive the user input directly on the standard view through the user input unit 430.

The storage unit 450 may store a predetermined template of available measurement information according to a type of the standard view. The image processor 420 may acquire one or more candidate groups with respect to the measurement information based on at least one of the user input received from the user input unit 430, the predetermined template, and the standard view. Scores with respect to one or more candidate groups may be acquired according to a similarity between the predetermined template and the standard view. A candidate group having the highest similarity with the predetermined template may be acquired as a final candidate group.

The ultrasound diagnosis apparatus 100 may further include the output unit 440 that outputs at least one of the one or more candidate groups and the acquired scores to the user. The user may see the output scores and select a most appropriate candidate group through the user input unit 430. The output unit 440 may output at least one of a generate ultrasound image, the standard view, the measurement information, and the measurement objects as at least one of an image, sound, and computer readable data.

Figure 5:
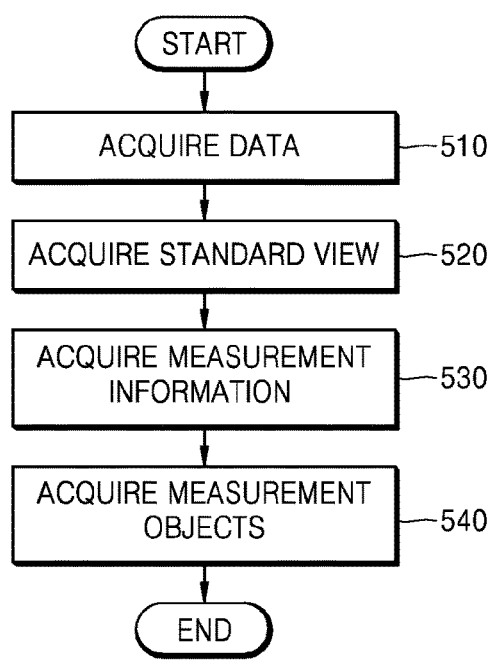
FIG. 5 is a flowchart of an ultrasound diagnosis method according to an embodiment of the present invention.

FIG. 5 is a flowchart of an ultrasound diagnosis method according to an embodiment of the present invention.

The ultrasound diagnosis method according to the present embodiment may include acquiring ultrasound data by performing ultrasonography on a target object (operation S510), generating an ultrasound image by using the ultrasound data, and acquiring a standard view based on the ultrasound image (operation S520), acquiring measurement information that is information regarding measurable measurement objects in the standard view based on the standard view (operation S530), and acquiring at least one of the measurement objects based on the acquired measurement information (operation S540). The ultrasound diagnosis method is redundant with the ultrasound diagnosis apparatus of FIG. 3, and thus a detailed description thereof is omitted.

FIGS. 6A and 6B are diagrams for comparing the related art and the present invention.

In more detail, FIG. 6A illustrates the conventional art that acquires (610) ultrasound data, and generates an ultrasound image by using the ultrasound data acquired by the data acquisition unit 310. A standard view is acquired based on the ultrasound image. A user selects (620) a measurement object that is to be measured on the standard view. For example, when a BPD is selected as a first measurement object, the user inputs a caliper on the standard view and acquires (630) the measurement object. When the user wants to measure an OFD as a second measurement object, the user selects (640) the OFD, inputs the caliper, and acquires (650) the second measurement object. The conventional art has an inconvenience that a plurality of user inputs are necessary for acquiring a single measurement object.

Unlike the conventional art, FIG. 6B illustrates the present invention. According to the present invention, ultrasound data is acquired (660), and then an ultrasound image is generated by using the ultrasound data acquired by the data acquisition unit 310. A standard view is acquired based on the ultrasound image. A user may acquire (670) a first measurement object without having to selecting a separate measurement object. The user may acquire a second measurement object according to a user input. The present invention may dramatically reduce user inputs compared to the conventional art.

Figure 7:
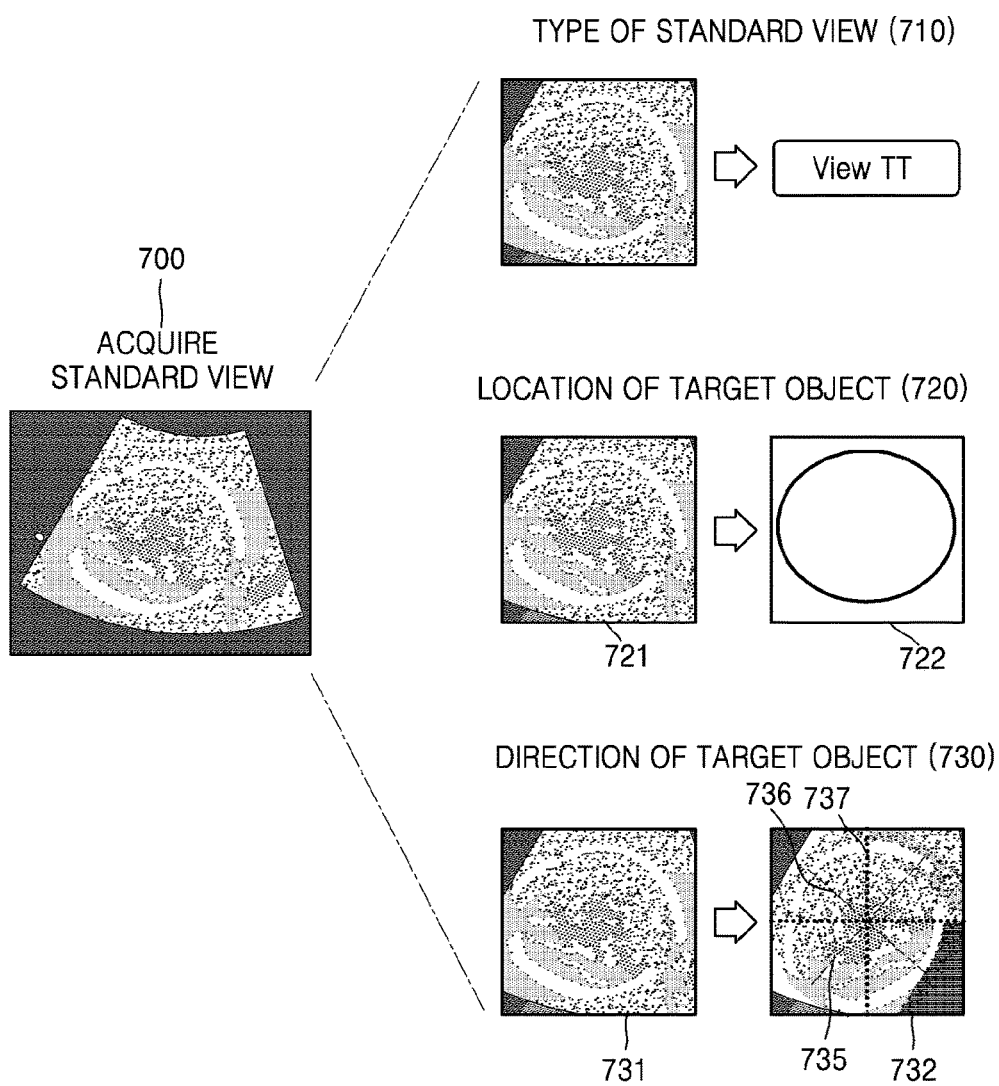
FIG. 7 is a diagram for explaining information that may be acquired along with a standard view according to an embodiment of the present invention.

FIG. 7 is a diagram for explaining information that may be acquired along with a standard view according to an embodiment of the present invention. In more detail, referring to FIG. 7, after acquiring the standard view, measurement information that may be acquired from the standard view is explained.

The standard view maybe acquired (700) along with information relating to the standard view. For example, measurement information including at least one of a type 710 of the standard view, a location 720 of a target object, and a direction 730 of the target object.

The standard view represents a cross-section of the target object necessary for diagnosing a state of the target object, a disease, etc., and thus the measurement object that may be acquired may be determined according to the type 710 of the standard view. FIG. 7 shows standard views with respect to the brain. A TT may be acquired as the type 710 of the standard view among the standard views with respect to the brain.

The location 720 of the target object may be acquired along with the standard view. Since the target object is not fixed, a location of the target object of the standard view may be different according to relative locations of a probe and the target object. For example, the image processor 420 may extract a boundary image 722 of the target object from the standard view by performing image processing such as outline improvement filtering on a TT standard view 721 regarding the brain. A location of the target object in an image may be acquired from the extracted boundary image 722 of the target object. Shape information of the target object may also be extracted from the extracted boundary image 722 of the target object. For example, an outline of the target object may be used as shape information in the boundary image 722 of the target object. Measurement information may be acquired based on the extracted shape information including the outline.

The direction 730 of the target object may be acquired along with the standard view. Since the target object is not fixed, the direction of the target object of the standard view may be different according to relative locations of the probe and the target object. For example, when a TT standard view 731 regarding the brain is acquired, the image processor 420 may acquire a major axis 735 and a minor axis 736 of the target object in the TT standard view 731, compare the acquired major axis 735 and minor axis 736 with a reference axis 737 on an image 732, and acquire the direction 730 of the target object such as how much the target object is inclined from the plane.

Figure 8:
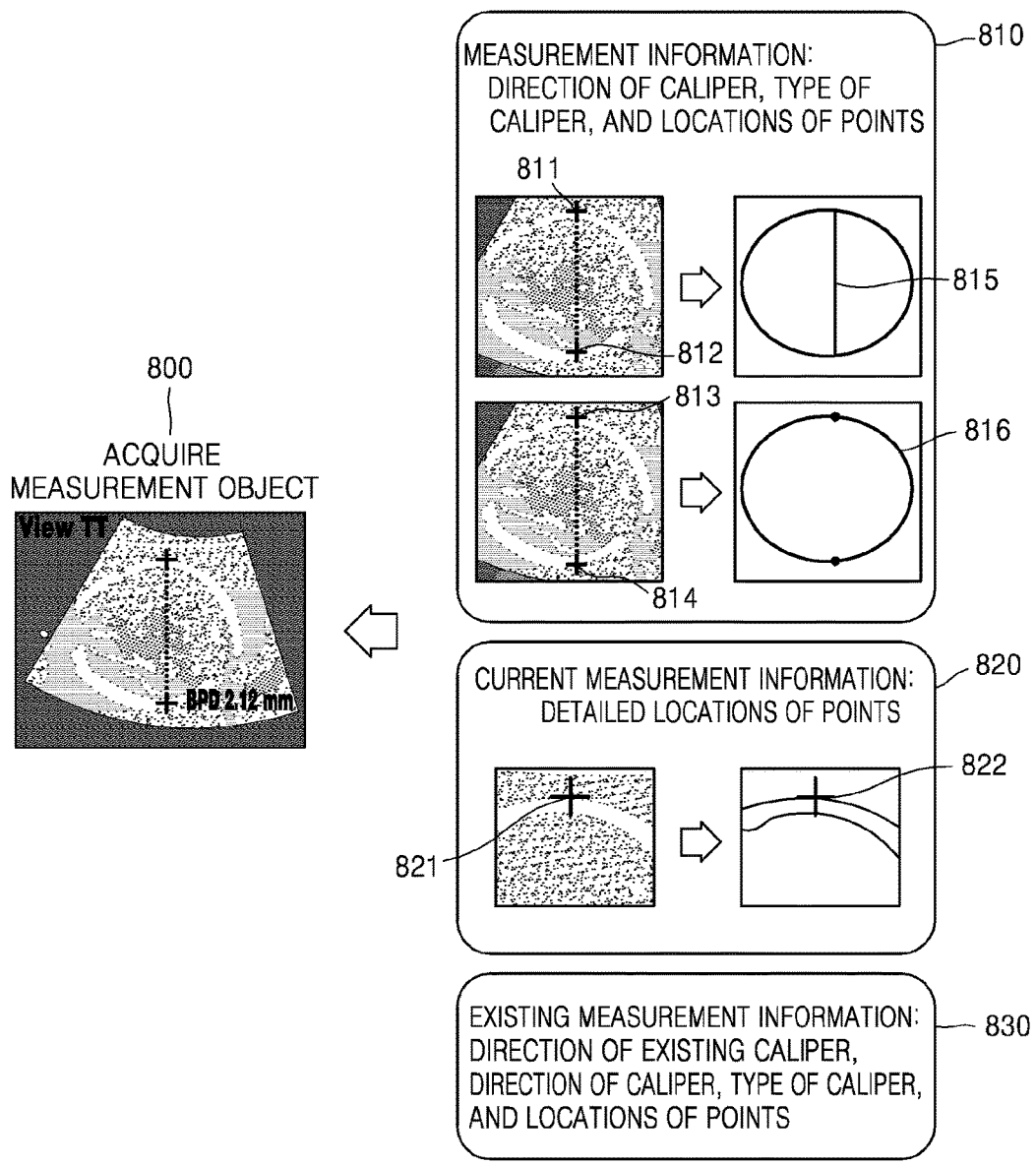
FIG. 8 illustrates various factors that may be used to acquire a measurement object according to an embodiment of the present invention.

FIG. 8 illustrates various factors that may be used to acquire a measurement object according to an embodiment of the present invention.

The image processor 420 may acquire a measurement object by determining whether predetermined measurement information is included in a range of measurement information corresponding to one of measurement objects. The measurement object may be acquired (800) based on the measurement information. The measurement information may include at least one of a direction of a caliper, a type, a location, and locations of points. For example, when the caliper is a straight line in a vertical direction, a BPD that is the straight line may be a measurement object.

The image processor 420 may extract shape information of a target object based on a standard view and acquire measurement information based on the extracted shape information. For example, a TT standard view represents axial section of a head. The shape information of the target object in the axial section of a head may be an oval outline. At least one of a circumference of the oval outline, a minor axis, and a major axis may be measured. Thus, at least one of the direction of the caliper, the type, the location, and the locations of the points may be acquired as the measurement information to measure at least one of the circumference of the oval outline, the minor axis, and the major axis. The BPD may be acquired as the measurement object based on the measurement information.

A block 810 represents the measurement information according to an embodiment of the present invention. The measurement information may be different according to the locations of the points included in the caliper. For example, when a point 811 is outside one side of the target object, and a point 812 is inside the opposite side of the target object, the measurement information may be information regarding a caliper 815 that is a vertical line indicating the BPD. When a point 813 is outside one side of the target object, and a point 814 is outside the opposite side of the target object, the measurement information may be information regarding an oval caliper 816 indicating a HC. The HC may be acquired as the measurement object based on the measurement information. The measurement information may be differently acquired according to the locations of the points.

A block 820 is an enlargement of the point 811 of the block 810. A point 821 is disposed on the standard view. However, since an image is unclear, it is unclear whether the point 821 is outside one side of the target object. The image processor 420 may perform image processing on the standard view. The image processor 420 may extract shape information from the standard view on which image processing is performed. For example, the image processor 420 may perform outline improvement processing on the standard view. An outline extracted from the standard view may be shape information. Since the outline is clearer through image processing, it may be more accurately determined that the point 821 is outside one side of the target object. The measurement information may be acquired according to locations of the points 811 through 814 based a determination result.

The measurement information may be acquired based on the shape information. In an embodiment, the point 821 may be acquired according to a user input. In this regard, as described with reference to the block 810 above, the measurement information may be different according to whether the point 821 is disposed in the point 812 or the point 814. The point 812 may be close to an inner outline of the target object. The point 814 may be close to an outer outline of the target object. That is, different measurement information may be acquired based on relative locations of the point 821 and the outline. The block 820 may enable to accurately determine that a point 822 is disposed on the outer outline of the target object on the extracted outline through image processing. The image processor 420 may acquire the measurement information based on the locations of the point 821 and the outline.

A block 830 shows that measurement information may be acquired by using existing measurement information according to an embodiment of the present invention. For example, when the user corrects the existing measurement information, the existing measurement information that is the closest to a location of an indicator input by the user may be corrected. In more detail, a location of an existing point that is the closest to the location of the indicator based on a user input may be corrected as the location of the indicator. The measurement object may be acquired based on the corrected location of the point.

Figure 22:
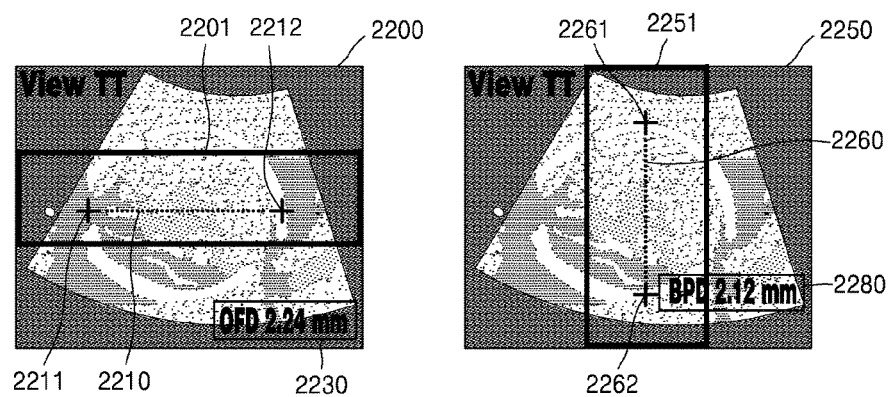
FIG. 22 illustrates ultrasound diagnosis screens for explaining a process of acquiring a measurement object based on measurement information according to an embodiment of the present invention.

FIG. 22 illustrates ultrasound diagnosis screens for explaining a process of acquiring a measurement object based on measurement information according to an embodiment of the present invention.

The image processor 420 may acquire the measurement object by determining whether the measurement information is included in a predetermined range of measurement information corresponding to the measurement object.

For example, an TT standard view 2200 may be a standard view regarding a head of a fetus. A caliper 2210 may be automatically acquired by the image processor 420 or may be acquired according to a user input. The caliper 2210 may be acquired based on points 2211 and 2212. The image processor 420 may determine whether the caliper 2210 that is measurement information is present within a range 2201 of measurement information corresponding to a measurement object. For example, the predetermined range 2201 may correspond to an OFD that is a measurement object with reference to the standard view 2200 of FIG. 22. When the caliper 2210 is present within the predetermined range 2201, the image processor 420 may acquire the OFD as the measurement object. A measurement value of the OFD acquired based on the caliper 2210 may be 2.47 mm. The measurement object and the measurement value may be displayed (2230) on an ultrasound image.

An TT standard view 2250 may be the standard view regarding the head of the fetus. A caliper 2260 may be automatically acquired by the image processor 420 or may be acquired according to the user input. The caliper 2260 may be acquired based on points 2261 and 2262. The image processor 420 may determine whether the caliper 2260 that is measurement information is present within a range 2251 of measurement information corresponding to a measurement object. For example, the predetermined range 2251 may correspond to a BFD that is a measurement object with reference to the standard view 2200 of FIG. 22. When the caliper 2260 is present within the predetermined range 2251, the image processor 420 may acquire the BFD as the measurement object. A measurement value of the BFD acquired based on the caliper 2260 may be 2.12 mm. The measurement object and the measurement value may be displayed (2280) on the ultrasound image.

The process of acquiring the measurement object based on the calipers 2210 and 2260 is described above but is not limited thereto. The image processor 420 may acquire the measurement object by determining whether measurement information including at least one of a direction of a caliper, a type, a location, and locations of points is included in a predetermined range of measurement information corresponding to the measurement object. For example, the measurement object may be acquired based on a directional range of the caliper inclined from a vertical line on a standard view, a distance range of a location of each point away from an outline of a target object, and a distance range of each point away from a specific point on the standard view.

Figure 9:
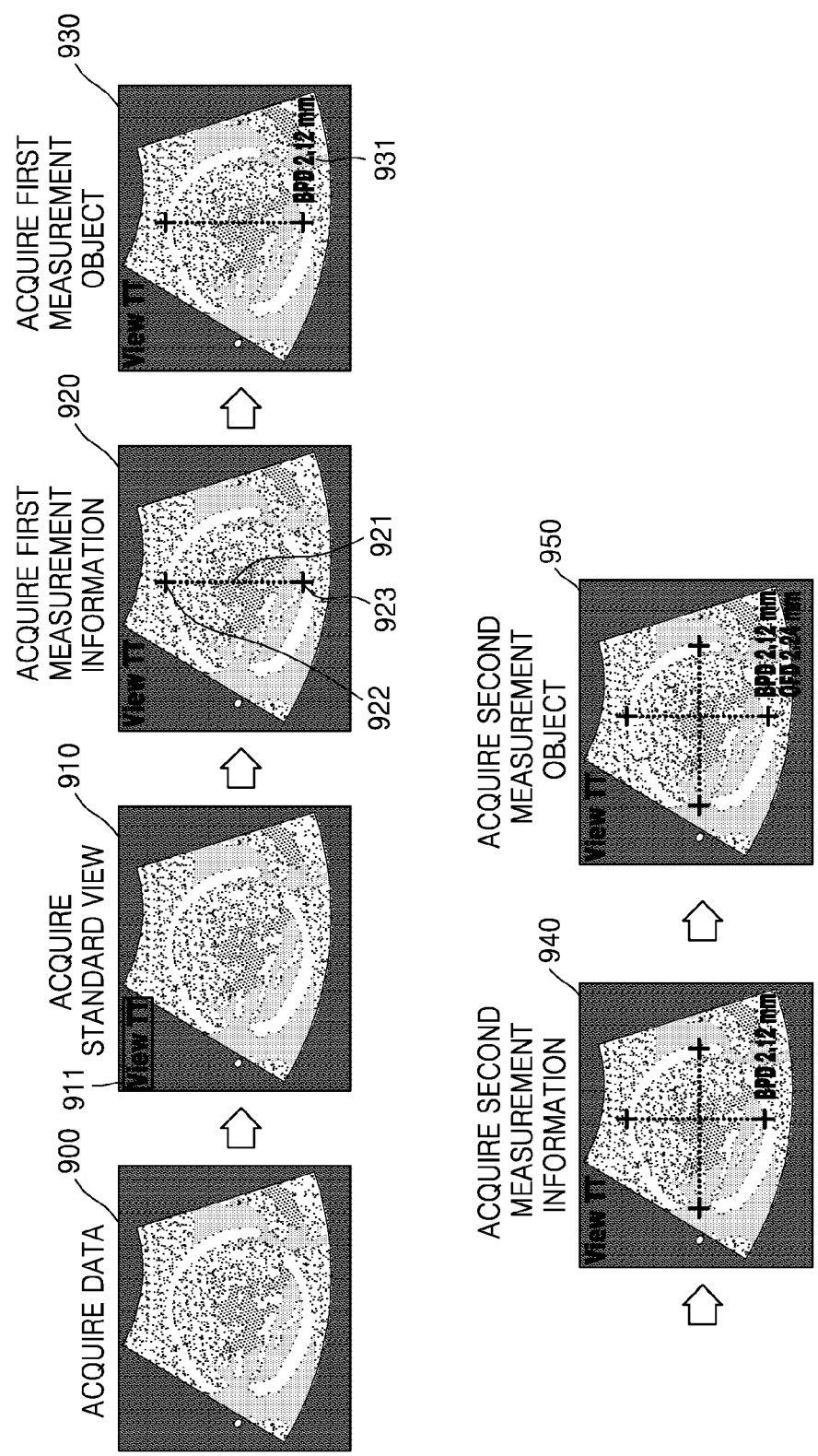
FIG. 9 illustrates ultrasound diagnosis screens showing a brain according to an embodiment of the present invention.

FIG. 9 illustrates ultrasound diagnosis screens showing a brain according to an embodiment of the present invention.

An ultrasound diagnosis apparatus may acquire ultrasound data of a cross-section of a brain by performing ultrasonography on the brain that is a target object. The ultrasound diagnosis apparatus may generate an ultrasound image 900 based on the acquired ultrasound data and acquire a standard view 910 based on the ultrasound image 900. The acquired standard view 910 may be displayed along with a type 911 of the standard view 910. For example, the type of the standard view 910 may be a TT. Next, the image processor 420 may automatically acquire first measurement information that is one of information regarding measurement objects measurable within the standard view 920 based on the standard view 920. For example, the image processor 420 may perform image processing such as outline improvement filtering on the TT standard view 920 and extract shape information of the measurement object. The extracted shape information may be an oval (i.e. an axial section of the head) outline. The image processor 420 may acquire information regarding a minor axis of the oval outline as the first measurement information. The first measurement information may be information in which a caliper 921 has a vertical direction, a point 922 is outside one side of the target object, a point 923 is inside the opposite side of the target object, and the caliper 921 is a straight line type. An ultrasound image 920 including the measurement information may be displayed. The image processor 420 may acquire a BPD as a first measurement object based on the first measurement information. A measurement value of the acquired first measurement object may be displayed (931) as "BPD:2.12 mm" on the standard view 930. An ultrasound image 930 including at least one of the acquired first measurement object and a measurement value may be displayed.

The image processor 420 may acquire second measurement information that is one of measurement objects that may be acquired within the standard view 940 in a similar way to acquiring the first measurement information. For example, the second measurement information may be information in which the caliper has a horizontal direction and is the straight line type. An OFD may be acquired as a second measurement object based on the second measurement information. An ultrasound image 950 including at least one of the first measurement information, the first measurement object, the second measurement information, the second measurement object, and the measurement value may be displayed.

Figure 10:
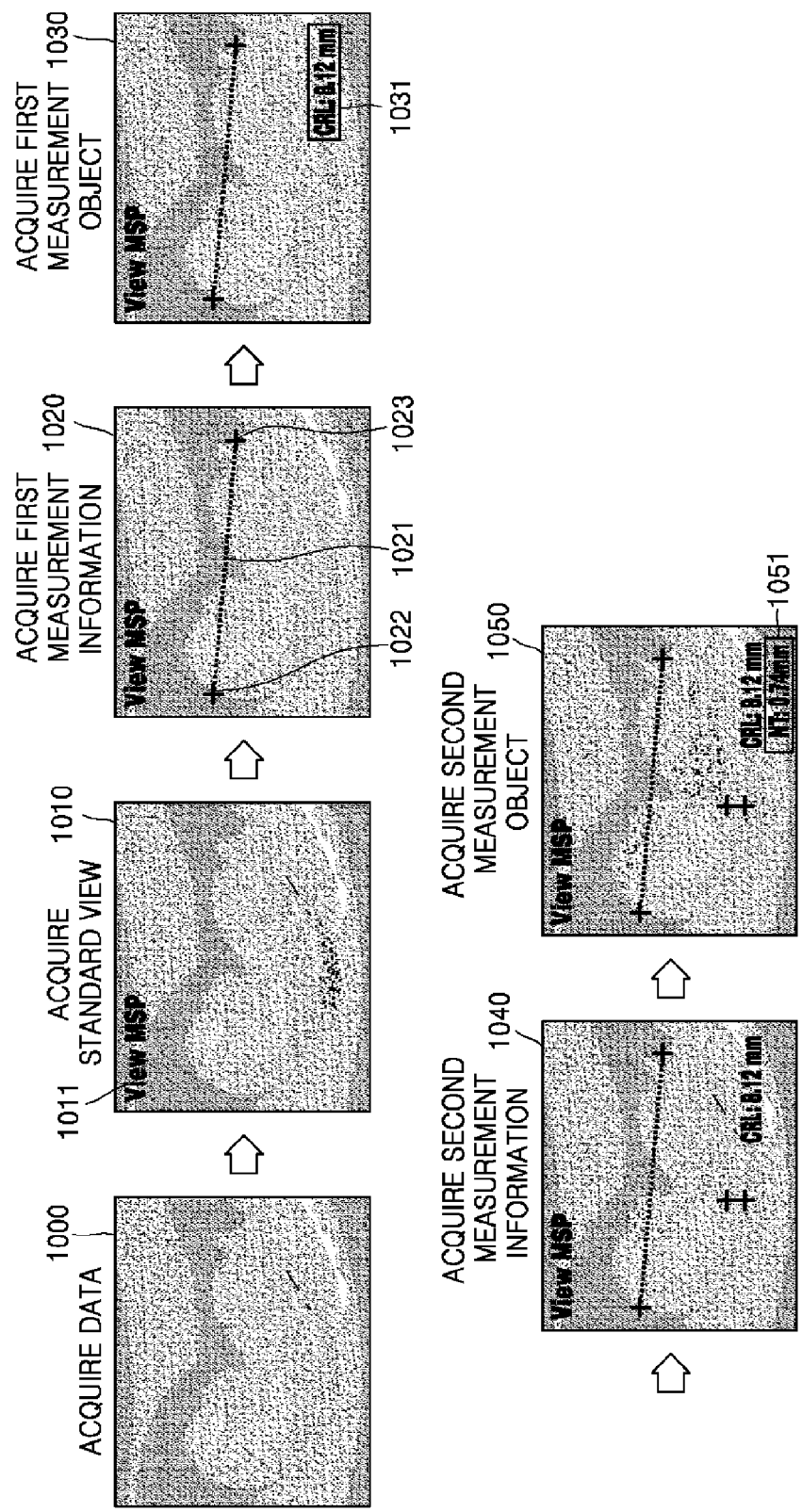
FIG. 10 illustrates ultrasound diagnosis screens showing a fetus according to an embodiment of the present invention.

FIG. 10 illustrates ultrasound diagnosis screens showing a fetus according to an embodiment of the present invention.

An ultrasound diagnosis apparatus may acquire ultrasound data of a cross-section of a fetus by performing ultrasonography on the fetus that is a target object. The ultrasound diagnosis apparatus may generate an ultrasound image 1010 based on the acquired ultrasound data and acquire a standard view 1010 based on the ultrasound image 1010. The acquired standard view 1010 may be displayed along with a type 1011 of the standard view 1010. For example, the type of the standard view 1010 may be an MSP. The image processor 420 may automatically acquire first measurement information that is one of information regarding measurement objects measurable within the standard view 1020 based on the standard view 1020. For example, the image processor 420 may perform image processing such as outline improvement filtering on the MSP standard view 1020 and extract shape information of the measurement object. The extracted shape information may be a shape derived from a midsagittal of the fetus. The image processor 420 may acquire information regarding a caliper 1021 having a crow point 1022 of the shape derived from the midsagittal of the fetus and a rump point 1023 as both edges as the first measurement information. The first measurement information may be information in which the caliper 1021 has a substantially horizontal direction and is a straight line type. The first measurement information may be information in which the point 1022 disposed in one side of the caliper 1021 is the crown, and the point 1023 disposed in another side thereof is the rump. An ultrasound image 2010 including the acquired measurement information may be displayed on an ultrasound image 1020.

A CRL may be acquired as a first measurement object based on the first measurement information. A measurement value of the acquired CRL may be displayed as "CRL:8.12 mm" (1031). An ultrasound image 1030 including the measurement object and the measurement value may be displayed. The image processor 420 may acquire second measurement information that is one of measurement objects that may be acquired within the standard view 1040 in a similar way to acquiring the first measurement information. For example, the second measurement information may be information in which the caliper has a vertical direction and is the straight line type. An ultrasound image 1040 including the acquired measurement object may be displayed. An NT may be acquired as a second measurement object based on the second measurement information. A measurement value of the NT may be displayed "NT:0.74 mm" (1051). An ultrasound image 1050 including at least one of the first measurement information, the first measurement object, the second measurement information, the second measurement object, and the measurement value may be displayed.

Figure 11:
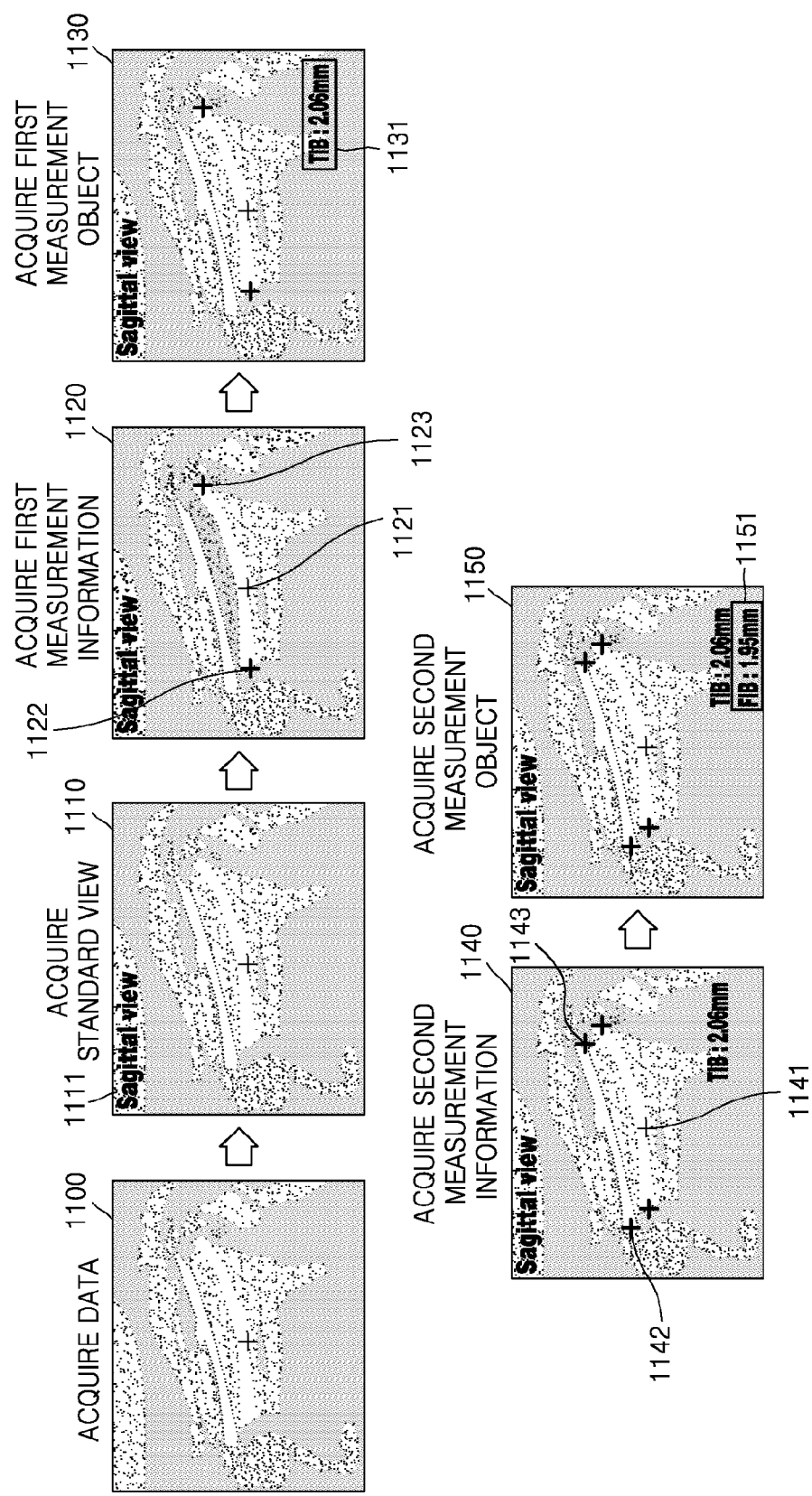
FIG. 11 illustrates ultrasound diagnosis screens according to an embodiment of the present invention.

FIG. 11 illustrates ultrasound diagnosis screens showing a bone according to an embodiment of the present invention.

An ultrasound diagnosis apparatus may acquire ultrasound data of a cross-section of a bone by performing ultrasonography on the bone that is a target object. The ultrasound diagnosis apparatus may generate an ultrasound image 1100 based on the acquired ultrasound data and acquire a standard view 1110 based on the ultrasound image 1100. The acquired standard view 1110 may be displayed along with a type 1111 of the standard view 1110. The image processor 420 may acquire first measurement information that is one of information regarding measurement objects measurable within the standard view 1120 based on the standard view 1120. For example, the image processor 420 may perform image processing such as outline improvement filtering on the sagittal standard view 1120 and extract shape information of the measurement object. The extracted shape information may be a shape of a leg bone of the fetus. The image processor 420 may acquire information regarding a caliper 1121 that connects both edges of the tibia of the leg bone of the fetus as the first measurement information. The first measurement information may be information in which the caliper 1121 has a substantially horizontal direction? am almost-horizontal direction and is a straight line type. The first measurement information may be information in which a point 1122 on the caliper 1121 may be disposed in one edge on the tibia and a point 1123 may be disposed in another edge on the tibia. The tibia may be acquired as a first measurement object based on the first measurement information. A measurement value of the acquired tibia may be displayed as "TIB:2.06 mm" (1131). An ultrasound image 1130 including at least one of the first measurement information and the measurement value of the acquired tibia may be displayed. Next, the image processor 420 may acquire second measurement information that is one of measurement objects that may be acquired within the standard view 1140 based on the standard view 1140. For example, the second measurement information may be information in which the caliper has a substantially horizontal direction? am almost-horizontal direction, the two points 1142 and 1143 are disposed on the fibula, and the caliper 1141 is the straight line type. An ultrasound image 1140 including the acquired second measurement object may be displayed. The fibula may be acquired as a second measurement object based on the second measurement information. A measurement value of the acquired second measurement object may be displayed "FIB:1.95 mm" (1151). An ultrasound image 1150 including at least one of the second measurement information and the measurement value of the acquired fibula may be displayed.

Figure 12:
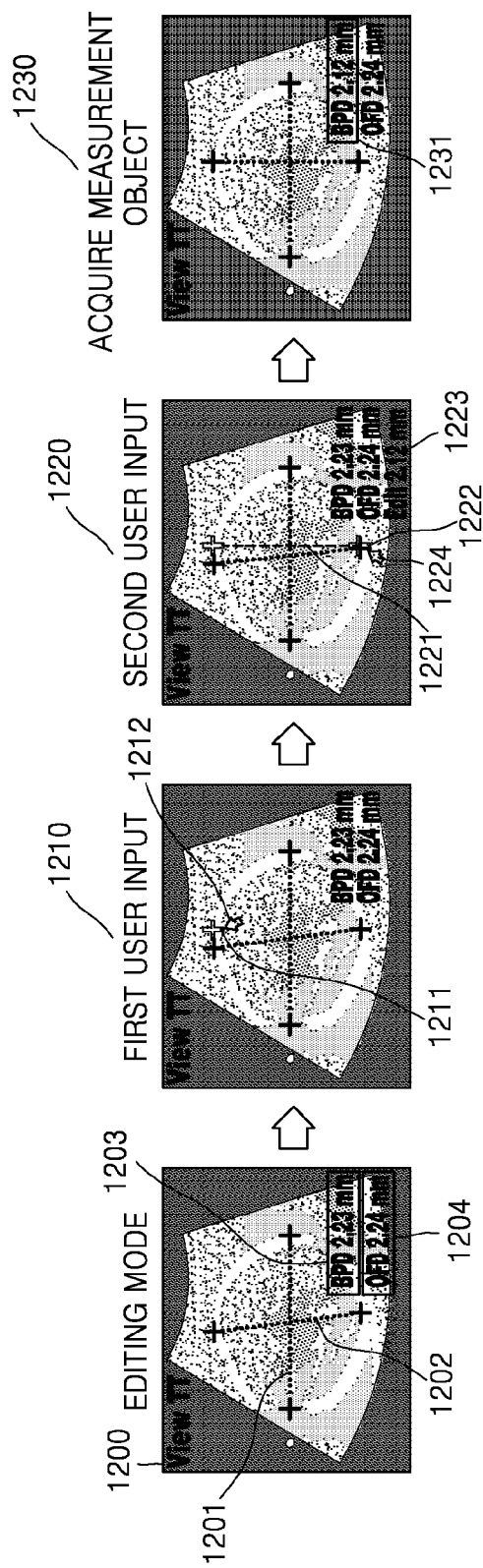
FIG. 12 illustrates ultrasound diagnosis screens for explaining a process of acquiring a measurement object based on a user input according to an embodiment of the present invention.

FIG. 12 illustrates ultrasound diagnosis screens for explaining a process of acquiring a measurement object based on a user input according to an embodiment of the present invention.

When a user personally wants to edit measurement information or the measurement object with respect to a standard view, the user may select an editing mode. When it is requested that the measurement information or the measurement object is edited through the user input unit 430, an image 1200 including an ultrasound image may be displayed. The image 1200 including the ultrasound image may include existing measurement information or measurement object. The existing measurement object included in the image 1200 may be a BPD 1203 with respect to a caliper 1201 in a vertical direction and an OFD 1204 with respect to a caliper 1202 in a horizontal direction. A case of acquiring the existing measurement object in FIG. 12 may include a case of acquiring the existing measurement object or a case of acquiring a measurement object according to an embodiment of the present invention as described with reference to FIG. 4 above.

The user may move an indicator 1212 on an ultrasound image 1210 indicating a standard view by using the user input unit 430. When the user selects a point 1211 by placing the indicator 1212 on the point 1211, the image processor 420 may acquire the point 1211 as a first user input. The ultrasound image 1210 that acquires the first user input may be displayed. Next, the user may move an indicator 1222 on the standard view by using the user input unit 430 again. When the user selects the point 1221 by placing the indicator 1222 on the point 1221, the image processor 420 may acquire the point 1222 as a second user input. The ultrasound image 1220 that acquires the second user input may be displayed. The image processor 420 may acquire a caliper 1221 in the vertical direction based on a first user input point 1225 and a second user input point 1222. An ultrasound diagnosis apparatus may display a length value 1223 measured by the caliper 1221 in the vertical direction. For example, the length value 1223 may be displayed as "Edit: 2.12 mm". An ultrasound image 1230 that acquires the measurement object may be displayed.

In an embodiment of the present invention, the caliper 1221 that is a straight line in the vertical direction means a BPD in a TT standard view. The image processor 420 may determine that an existing BPD is edited as a BPD based on a user input in a direction of the caliper 1221 in the vertical direction. That is, the ultrasound diagnosis apparatus may acquire the measurement object as the BPD based on the first and second user inputs. A measurement value of the BPD may be corrected (1231) based on the measured length value 1223.

In another embodiment of the present invention, the user may change at least one piece of measurement information based on at least one of user inputs received to change measurements object and previously acquired measurement information. The measurement objects may be acquired based on the changed measurement information. For example, the user may execute an editing mode to change the measurement object. Changing of the measurement object includes complete changing of the measurement object and changing of a measurement value of the same measurement object. The caliper 1221 in the vertical direction based on the first and second user inputs is closest to the existing caliper 1202 in the vertical direction, and thus the existing caliper 1202 may be changed to the caliper 1221 based on the user inputs. The ultrasound diagnosis apparatus may acquire the BPD as the measurement object based on the first and second user inputs and the existing measurement information.

Figure 13:
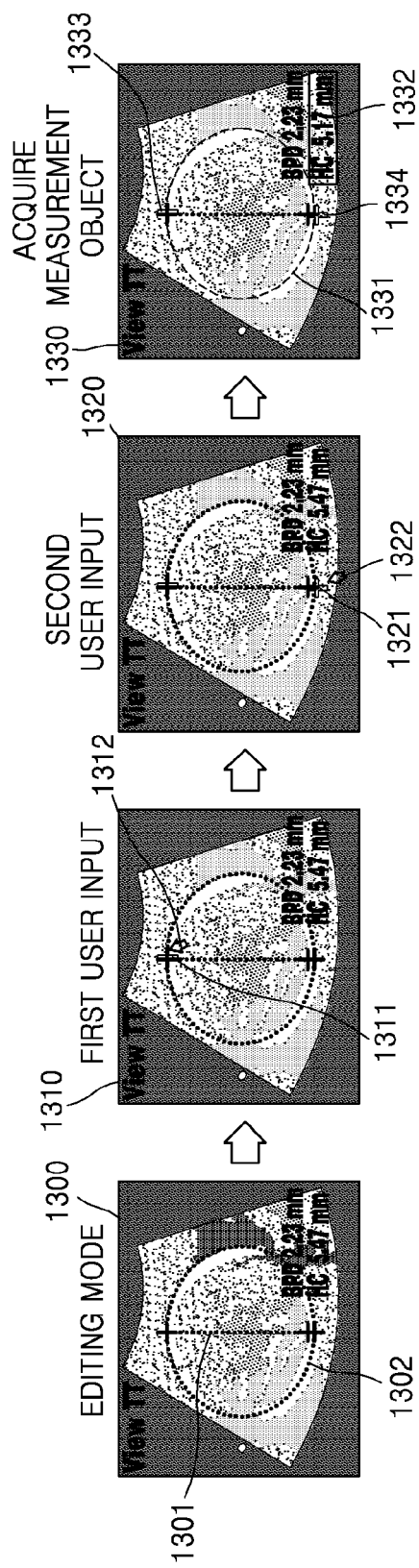
FIG. 13 illustrates ultrasound diagnosis screens for explaining a process of acquiring a measurement object based on a user input according to an embodiment of the present invention.

FIG. 13 illustrates ultrasound diagnosis screens for explaining a process of acquiring a measurement object based on a user input according to an embodiment of the present invention.

When a user personally wants to edit measurement information or the measurement object with respect to a standard view, the user may select an editing mode. When it is requested that the measurement information or the measurement object is edited through the user input unit 430, an image 1300 including an ultrasound image may be displayed. The image 1200 including the ultrasound image may include existing measurement information or measurement object. The existing measurement object included in the image 1200 may be a BPD with respect to a caliper 1301 in a vertical direction and an HC with respect to an oval caliper 1302 in a horizontal direction. A case of acquiring the existing measurement object in FIG. 13 may include a case of acquiring the existing measurement object or a case of acquiring a measurement object according to an embodiment of the present invention as described with reference to FIG. 5 above.

The user may move an indicator 1312 on an ultrasound image 1310 indicating a standard view by using the user input unit 430. When the user selects a point 1311 by placing the indicator 1312 on the point 1311, the image processor 420 may acquire the point 1311 as a first user input 1333. The ultrasound image 1310 that acquires the first user input may be displayed. Continuously, the user may move an indicator 1322 on the standard view by using the user input unit 430 again. When the user places the indicator 1322 on the point 1321, the image processor 420 may acquire the point 1321 as a second user input 1334. The ultrasound image 1320 that acquires the second user input may be displayed.

In an embodiment of the present invention, as described with reference to FIG. 8 above, when locations of first and second user inputs are respectively outside one side of a target object and inside the opposite side thereof, the measurement object may be the BPD. When the locations of first and second user inputs are respectively outside one side of a target object and outside the opposite side thereof, the measurement object may be the HC. The first user input 1333 of FIG. 13 is disposed outside one side of the target object in a white color on the standard view. The second user input 1334 of FIG. 13 is disposed outside the opposite side of the target object in the white color on the standard view. Thus, the image processor 420 may acquire an oval caliper 1331 based on the first user input 1333 and the second user input 1334. The image processor 420 may acquire the measurement object as the HC based on the first user input 1333 and the second user input 1334.

The ultrasound diagnosis apparatus may measure a circumference of the oval caliper 3331 and correct a measurement value of the HC. The measurement value of the HC may be, for example, "HC:5.17 mm". Accordingly, an image 1330 indicating the corrected measurement value of the HC may be displayed. A determined value 1332 of HC may be displayed as "HC:5.17 mm" on the image 1330.

Figure 14:
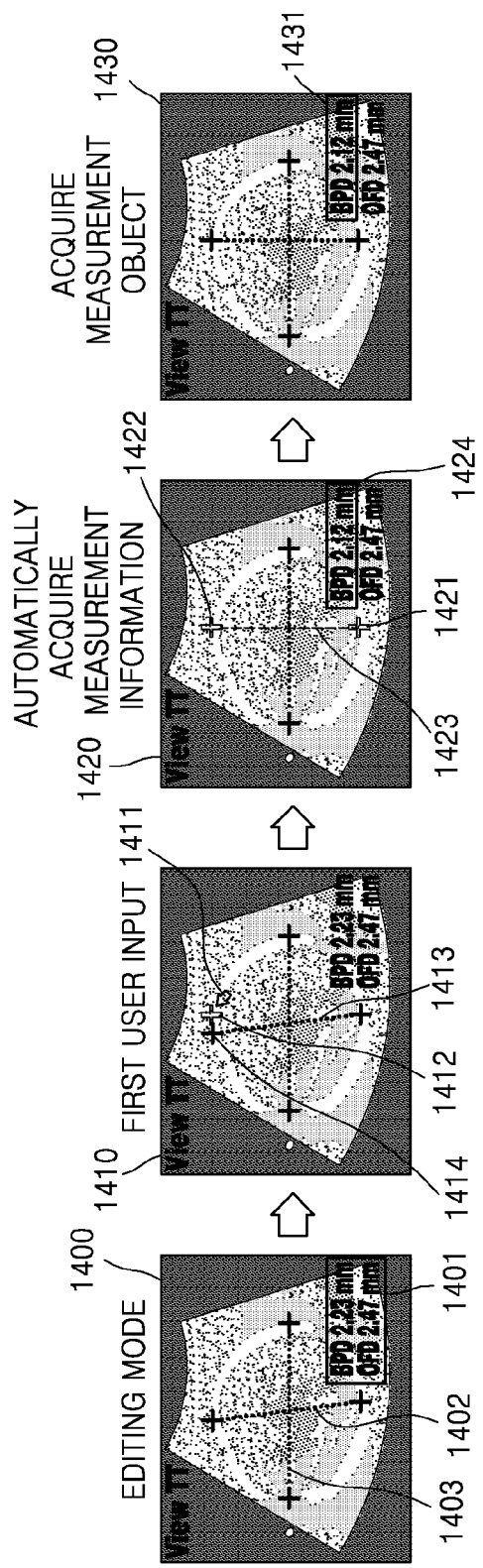
FIG. 14 illustrates ultrasound diagnosis screens for explaining a process of acquiring a measurement object based on a user input according to an embodiment of the present invention.

FIG. 14 illustrates ultrasound diagnosis screens for explaining a process of acquiring a measurement object based on a user input according to an embodiment of the present invention.

When a user personally wants to edit measurement information or the measurement object with respect to a standard view, the user may select an editing mode. When it is requested that the measurement information or the measurement object is edited through the user input unit 430, an image 1400 including an ultrasound image may be displayed. The image 1400 including the ultrasound image may include existing measurement information or measurement object. The existing measurement object included in the image 1400 may be a BPD 1402 with respect to a caliper in a vertical direction and an OFD 1403 with respect to a caliper in a horizontal direction. Measurement values of the BPD 1402 and the OFD 1403 may be displayed on a predetermined part 1401 of the image 1400. A case of acquiring the existing measurement object in FIG. 14 may include a case of acquiring the existing measurement object or a case of acquiring a measurement object according to an embodiment of the present invention as described with reference to FIG. 5 above.

The user may move an indicator 1411 on an ultrasound image 1410 indicating a standard view by using the user input unit 430. When the user selects a point 1412 by placing the indicator 1411 on the point 1412, the image processor 420 may acquire the point 1412 as a first user input. The ultrasound image 1410 that acquires the first user input may be displayed.

The image processor 420 may automatically acquire the measurement information based on the point 1412 of the first user input. The image processor 420 may automatically acquire a candidate group of available measurement information based on the point 1412 of the first user input. The image processor 420 may automatically select a candidate from the candidate group as the measurement information. The candidate may be selected from the candidate group in random and according to a predetermined priority. For example, the image processor 420 may acquire an available candidate group based on the point 1412 of the first user input and automatically select information regarding a caliper 1423 as the measurement information. The image processor 420 may acquire the BPD 1402 as the measurement object based on the new caliper 1423. The BPD 1402 may be automatically measured again. The image processor 420 may control a measurement value of the BPD 1402 that is measured again to be displayed (1424) on a screen. For example, the measurement value of the BPD 1402 that is measured again may be 2.12 mm. Accordingly, an image 1430 indicating the measurement value of the BPD 1402 may be displayed. A determined measurement value 1431 of the BPD 1402 may be displayed on the image 1430.

In another embodiment of the present invention, the image processor 420 may automatically acquire the measurement information based on a location of the first user input and existing measurement information. For example, the user may execute an editing mode to change the measurement object. Changing of the measurement object includes complete changing of the measurement object and changing of a measurement value of the same measurement object. When the user enters the first user input, an ultrasound diagnosis apparatus may change measurement information of an existing caliper 1413 closest to the first user input. For example, the point 1412 of the first user input is closest to the existing caliper 1413, and thus the image processor 420 may change the existing caliper 1413. That is, a point 1414 of the existing caliper 1413 may be changed to the point 1412 of the first user input. The existing caliper 1413 may be changed to the new caliper 1423 based on the point 1412 of the first user input and the point 1421 included in the existing measurement information. The image processor 420 may acquire the BPD 1402 as the measurement object based on the changed caliper 1423.

The BPD 1402 may be automatically measured again. The image processor 420 may control a measurement value of the BPD 1402 that is measured again to be displayed (1424) on the screen. For example, the measurement value of the BPD 1423 that is measured may be 2.12 mm. Accordingly, the image 1430 indicating the measurement value of the BPD 1423 may be displayed. A determined measurement value 1431 of the BPD 1423 may be displayed on the image 1430.

Figure 15:
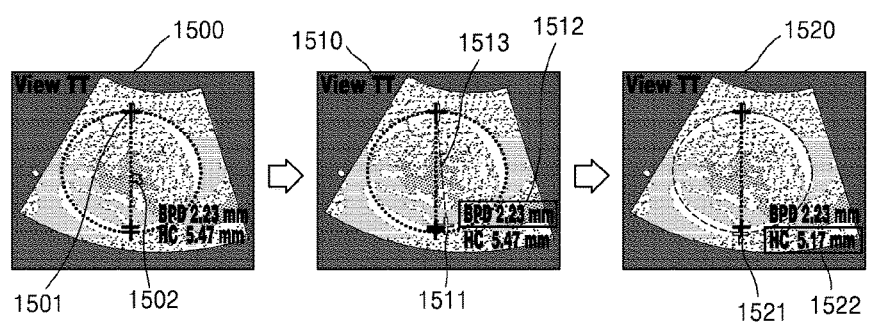
FIG. 15 illustrates ultrasound diagnosis screens for explaining a process of acquiring a measurement object based on a user input according to an embodiment of the present invention.

FIG. 15 illustrates ultrasound diagnosis screens for explaining a process of acquiring a measurement object based on a user input according to an embodiment of the present invention.

When a user personally wants to edit measurement information or the measurement object with respect to a standard view, the user may select an editing mode. When it is requested that the measurement information or the measurement object is edited through the user input unit 430, an image 1500 including an ultrasound image may be displayed. The image 1500 including the ultrasound image may include existing measurement information or measurement object. The existing measurement object included in the image 1500 may be a BPD with respect to a caliper in a vertical direction and an HC with respect to an oval caliper. Measurement values of the BPD 1402 and the OFD 1403 may be displayed on a predetermined part 1401 of the image 1400. A case of acquiring the existing measurement object in FIG. 15 may include a case of acquiring the existing measurement object or a case of acquiring a measurement object according to an embodiment of the present invention as described with reference to FIG. 5 above.

The user may move an indicator 1502 on a standard view by using the user input unit 430. When the user selects a point 1501 by placing the indicator 1502 on the point 1501, the image processor 420 may acquire the point 1501 as a first user input. The ultrasound image 1500 including the acquired first user input point 1501 and the indicator 1502 may be displayed. As shown in FIG. 15, the first user input point 1501 is disposed outside one side of a target object. Next, the user may move the indicator 1502 on the standard view in real time by using the user input unit 430. A caliper 1503 may be acquired based on the first user input point 1501 and the indicator 1502. Since the indicator 1502 is moved in real time, a measurement caliper 1513 may be changed in real time. The indicator 1502 may be disposed on a point 1511. The indicator 1502 disposed on the point 1511 is disposed inside the opposite side of the target object, and thus the image processor 420 may acquire the measurement information such as location information of the caliper in real time. The image processor 420 may acquire the BPD as the measurement object based on the measurement information. In this case, although there is no user selection, the image processor 420 may acquire the BPD as the measurement object only according to the indicator 1502 disposed on the point 1511. The image processor 420 may acquire a measurement value of the BPD in real time and reflect (1512) the measurement value. For example, the measurement value of the BPD may be "BPD:2.23 mm".

The indicator 1502 may be disposed on a point 1521. The indicator 1502 disposed on the point 1521 is outside the opposite side of the target object, and thus an ultrasound diagnosis apparatus may acquire the HC as the measurement object. In this case, although there is no user selection, the image processor 420 may acquire the HC as the measurement object only according to the indicator 1502 disposed on the point 1521. The image processor 420 may acquire a measurement value of the HC in real time and reflect (1522) the measurement value. For example, the measurement value of the HC may be "HC:5.17 mm".

Figure 16:
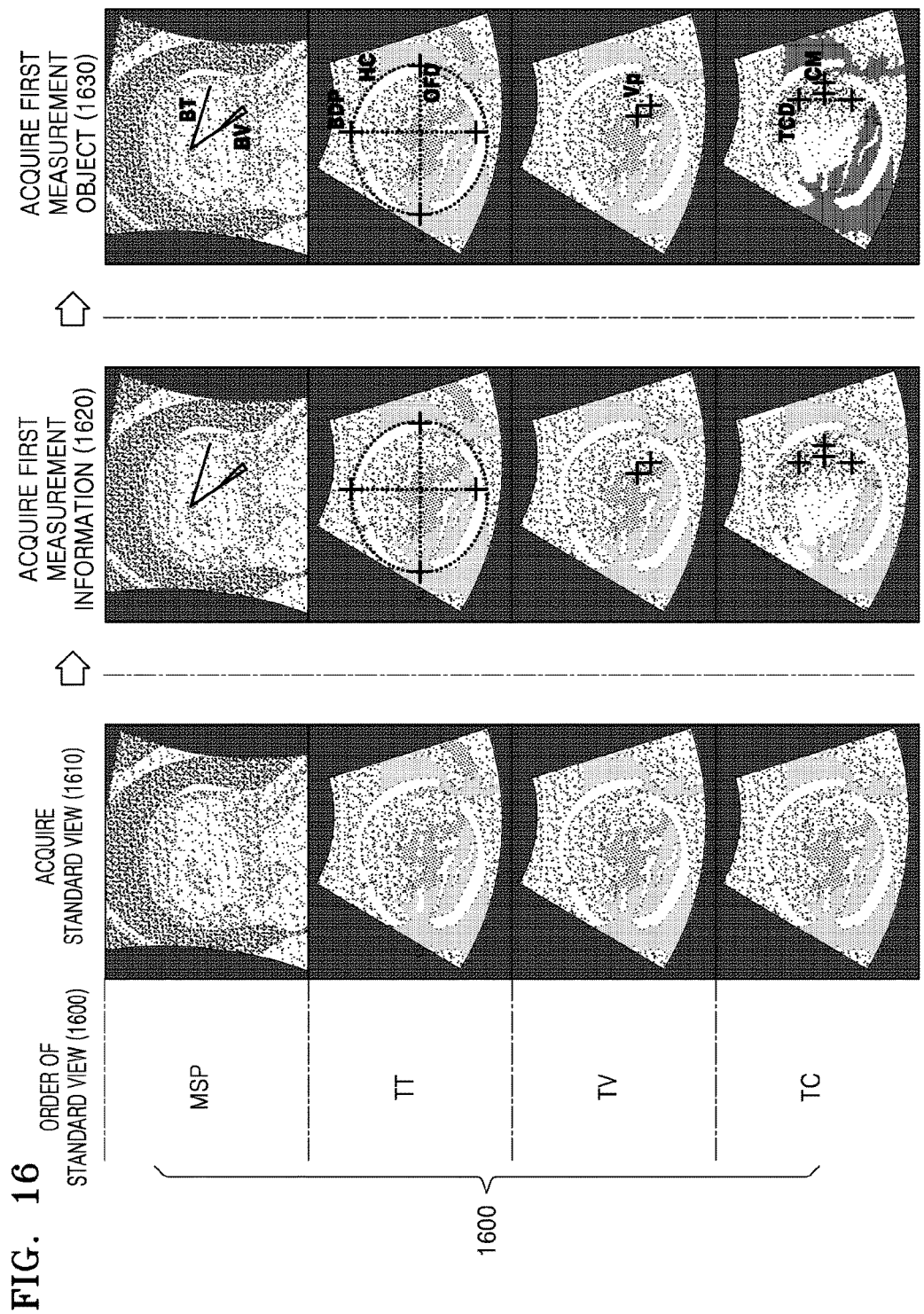
FIG. 16 illustrates ultrasound diagnosis screens for explaining a process of acquiring a measurement object with respect to each of a plurality of standard views according to an embodiment of the present invention.

FIG. 16 illustrates ultrasound diagnosis screens for explaining a process of acquiring a measurement object with respect to each of a plurality of standard views 1600 according to an embodiment of the present invention.

The image processor 420 may acquire the standard views 1600. The standard views 1600 may be loaded from a storage medium. The standard views 1600 may have priorities. When the standard views 1600 have no priority, the image processor 420 may automatically generate an order of the standard views 1600. Alternatively, a measurement object may be acquired for each of the standard views 1600. The measurement objects may be in parallel acquired. In FIG. 16, the standard views 1600 may be acquired in the order of MSP, TT, TV, TC, etc. The standard views 600 may be acquired (1610) based on the order of the standard views 1600, first measurement information may be acquired (1620) based on each of the standard views 1600, and a first measurement object may be acquired (1630) based on the first measurement information.

Figure 18:
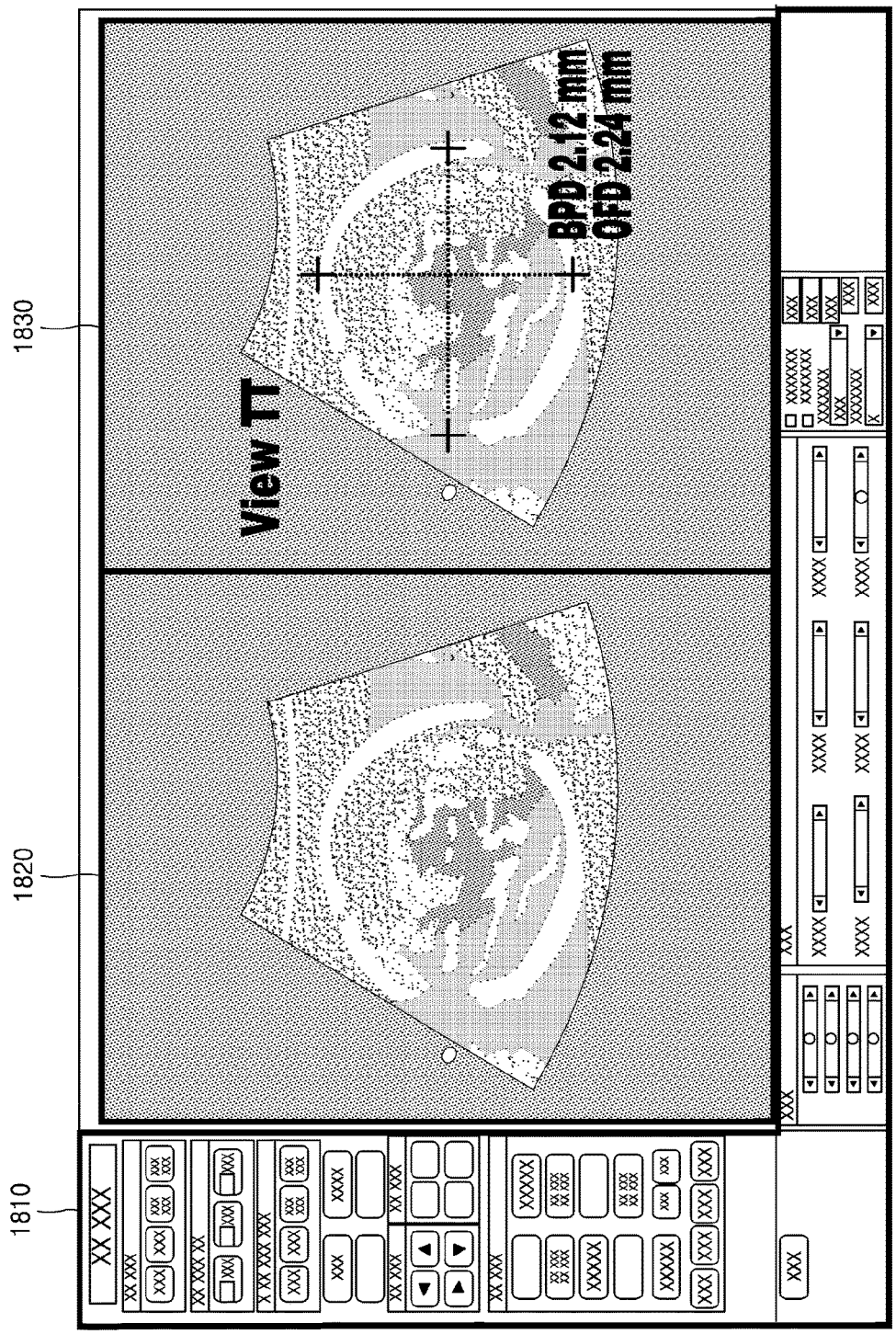
FIG. 18 illustrates of an example of an operation screen of the present invention.

FIG. 18 illustrates an example of an operation screen of the present invention.

A user does not need to select a measurement object personally, and thus the operation screen of the present invention may be simpler to use than that of the related art. Various menus 1810 may be output on the operation screen. A region 1820 may output an ultrasound image. A region 1830 may output a standard view based on the region 1820. At least one of acquired measurement information and measurement object may be displayed on the standard view. The measurement object and measurement information may overlap with each other according to an acquisition order and may be displayed.

FIG. 20 illustrates ultrasound diagnosis screens for explaining a process of acquiring a measurement object according to an embodiment of the present invention.

An ultrasound diagnosis apparatus may acquire (2000) a standard view. For example, the standard view may be a TT. Next, image processing may be performed on the acquired standard view such that the ultrasound diagnosis apparatus may easily acquire the standard view. For example, the ultrasound diagnosis apparatus may perform filtering (2010) on the acquired standard view. For example, the filtering (2010) may include outline improvement filtering. An outline on the standard view may be made more sharp by performing the filtering (2010). The ultrasound diagnosis apparatus may acquire (2020) measurement information based on a filtered image 2023. The measurement information may be acquired by comparing (2021) a template 2022 stored in a storage unit and the filtered image 2023. For example, the ultrasound diagnosis apparatus may compare the filtered image 2023 and the stored template 2022 in terms of at least one of relative locations, size, and angle. The ultrasound diagnosis apparatus may acquire a candidate group of measurement information by comparing the filtered image 2023 and the stored template 2022 in terms of at least one of relative locations, size, and angle. The ultrasound diagnosis apparatus may acquire (2027) a score of the candidate group according to a similarity between the filtered image 2023 and the stored template 2022. For example, if three candidate group 2024, 2025, and 2026 are acquired, the ultrasound diagnosis apparatus may acquire a score of the first candidate 2024 as 98, a score of the second candidate 2025 as 96, and a score of the third candidate 2026 as 92. The ultrasound diagnosis apparatus may output (2030) a result of displaying the candidate group 2024, 2025, and 2026 on a display apparatus. At least one of unique numbers of candidate group and similarity scores and an ultrasound image may be simultaneously output as the result. A user may select (2040) appropriate measurement information from the candidate group. For example, when the user selects the second candidate 2025, the ultrasound diagnosis apparatus may acquire a measurement object by selected the second candidate 2025 as the measurement information and output (2050) an acquisition result. A measurement value of the measurement object may be also acquired.

FIG. 21 illustrates ultrasound diagnosis screens for explaining a process of acquiring a measurement object according to another embodiment of the present invention.

An ultrasound diagnosis apparatus may acquire (2100) a standard view. For example, the standard view may be a TT. Next, image processing may be performed on the acquired standard view such that the ultrasound diagnosis apparatus may easily acquire the standard view. For example, the ultrasound diagnosis apparatus may perform filtering (2110) on the acquired standard view. For example, the filtering (2110) may include outline improvement filtering. An outline on the standard view may be made more sharp by performing the filtering (2110). The ultrasound diagnosis apparatus may acquire (2120) measurement information based on a filtered image 2123. The measurement information may be acquired by comparing (2121) a template 2122 stored in a storage unit and the filtered image 2123. For example, the ultrasound diagnosis apparatus may compare the filtered image 2123 and the stored template 2122 in terms of at least one of relative locations, size, and angle. The ultrasound diagnosis apparatus may acquire a candidate group of measurement information by comparing the filtered image 2123 and the stored template 2122 in terms of at least one of relative locations, size, and angle. The ultrasound diagnosis apparatus may acquire (2127) a score of the candidate group according to a similarity between the filtered image 2123 and the stored template 2122. For example, if three candidate group 2124, 2125, and 2126 are acquired, the ultrasound diagnosis apparatus may acquire a score of the first candidate 2124 as 98, a score of the second candidate 2125 as 96, and a score of the third candidate 2126 as 92. The ultrasound diagnosis apparatus may automatically select a most appropriate result from the candidate group 2024, 2025, and 2026 and output (2130) a selection result on a display apparatus. At least one of unique numbers of candidate group and similarity scores and an ultrasound image may be simultaneously output as the result. A user may correct (2140) a candidate group that is automatically selected by the ultrasound diagnosis apparatus. In this regard, the ultrasound diagnosis apparatus may propose (2141) the previously acquired candidate group to the user. For example, the ultrasound diagnosis apparatus may simultaneously output the acquired candidate group 2124, 2125, and 2126 on the display apparatus. At least one of unique numbers of candidate group and similarity scores and the ultrasound image may be simultaneously output as the result. The user may select (2142) a most appropriate candidate from the candidate group. For example, when the user selects the second candidate 2125, the ultrasound diagnosis apparatus may acquire a measurement object by selecting the second candidate 2125 as the measurement information and output (2150) an acquisition result. A measurement value of the measurement object may be also acquired.

The invention can also be embodied as computer readable codes on a computer readable recording medium. The computer readable recording medium is any data storage device that can store data which can be thereafter read by a computer system. Examples of the computer readable recording medium include read-only memory (ROM), random-access memory (RAM), CD-ROMs, magnetic tapes, floppy disks, optical data storage devices, etc. The computer readable recording medium can also be distributed over network coupled computer systems so that the computer readable code is stored and executed in a distributed fashion.

While this invention has been particularly shown and described with reference to embodiments thereof, it will be understood by those of ordinary skill in the art that various changes in form and details may be made therein without departing from the spirit and scope of the invention as defined by the appended claims. The embodiments should be considered in a descriptive sense only and not for purposes of limitation. Therefore, the scope of the invention is defined not by the detailed description of the invention but by the appended claims, and all differences within the scope will be construed as being included in the present invention.

What is claimed is:

1. An ultrasound diagnosis apparatus comprising:
   a data acquisition unit to acquire ultrasound data of a target object; and
   an image processor to:
     generate an ultrasound image by using the ultrasound data,
     acquire a standard view representing a plane of the target object including at least one of measurement objects used to diagnose the target object based on the ultrasound image, and information related to the standard view, the information comprising at least one among a type of the standard view, a location of the target object, and a direction of the target object,
     set a caliper to measure the target object on the standard view, based on a user input,
     acquire measurement information including caliper information of a position of the caliper and at least one point on the caliper, based on the standard view, and
     automatically acquire the at least one of the measurement objects being measured to diagnose the target object, based on the caliper information indicating that the caliper is inclined from a predetermined line on the standard view by a value that is within a first range, and that the at least one point on the caliper is away from a predetermined point in the standard view by a value that is within a second range,
   wherein the image processor is further configured to acquire the measurement objects by determining whether the caliper is inclined by a value that is within the first range, or the at least one point on the caliper is away from the predetermined point by a value that is within the second range.

2. The ultrasound diagnosis apparatus of claim 1, further comprising:
   a user input unit to receive user inputs on the acquired standard view.

3. The ultrasound diagnosis apparatus of claim 2, wherein the received user inputs are point information on the standard view, and
   wherein the image processor acquires the measurement information based on the received user inputs.

4. The ultrasound diagnosis apparatus of claim 2, wherein the image processor changes at least one of the measurement information based on at least one among the received user inputs for changing the measurement objects and the acquired measurement information and acquires the measurement objects, based on the changed measurement information.

5. The ultrasound diagnosis apparatus of claim 4, wherein an indicator corresponds to the received user inputs, and the changed measurement information is acquired based on a location of the indicator on the standard view and the acquired measurement information.

6. The ultrasound diagnosis apparatus of claim 2, wherein the image processor acquires the measurement information and the measurement objects in real time according to the user inputs.

7. The ultrasound diagnosis apparatus of claim 2, further comprising:
   a storage unit to store a predetermined template of the measurement information according to the type of the standard view, wherein the image processor acquires one or more candidate groups with respect to the measurement information based on at least one among the received user inputs, the predetermined template, and the standard view.

8. The ultrasound diagnosis apparatus of claim 7, wherein the image processor acquires scores of the one or more candidate groups according to a similarity between the predetermined template and the standard view.

9. The ultrasound diagnosis apparatus of claim 8, further comprising:
an output unit to output at least one among the one or more candidate groups and the acquired scores to a user.

10. The ultrasound diagnosis apparatus of claim 1, wherein the image processor extracts shape information of the target object based on the standard view and acquires the measurement information based on the extracted shape information including an outline.

11. The ultrasound diagnosis apparatus of claim 10, wherein the image processor comprises a filter for clearly displaying a characteristic of the standard view to extract the shape information of the target object.

12. The ultrasound diagnosis apparatus of claim 1, further comprising:
an output unit to output at least one among the generated ultrasound image, the standard view, the measurement information, and the measurement objects as at least one among an image, sound, and computer readable data.

13. The ultrasound diagnosis apparatus of claim 1, wherein the image processor automatically acquires the measurement information based on at least one among the type of the standard view, the location of the target object, and the direction of the target object.

14. The ultrasound diagnosis apparatus of claim 1, wherein the image processor acquires a plurality of standard views and acquires the measurement objects corresponding to each of the plurality of standard views.

15. The ultrasound diagnosis apparatus of claim 1, further comprising:
a storage unit to store a predetermined template of the measurement information according to the type of the standard view,
wherein the image processor acquires one or more candidate groups regarding the measurement information, based on at least one among the predetermined template and the standard view.

16. The ultrasound diagnosis apparatus of claim 15, wherein the image processor acquires scores of the one or more candidate groups according to a similarity between the predetermined template and the standard view.

17. The ultrasound diagnosis apparatus of claim 16, further comprising:
an output unit to output at least one among the one or more candidate groups and the acquired scores to a user.

18. The ultrasound diagnosis apparatus of claim 1, wherein the standard view comprises at least one among Training, a Harr pattern, and Sobel detection.

19. The ultrasound diagnosis apparatus of claim 1, wherein the standard view comprises at least one among a mid-sagittal plane, a transventricle plane, a transthalamic plane, a transcerebellar plane, a four-chamber view, a five chamber view, a three vessel view, an RVOT (Right Ventricular Outflow Tract), an LVOT (Left Ventricular Outflow Tract), a bicaval view, an aortic arch, a ductal arch, a high short axis view, and a low short axis view.

20. The ultrasound diagnosis apparatus of claim 1, wherein the measurement information comprises at least one among a direction of the caliper, a location of the caliper, a type of the caliper, and location information of points of the caliper.

21. The ultrasound diagnosis apparatus of claim 1, wherein the measurement objects comprise at least one among CRL (Crown-rump length), NT (Nuchal translucency), IT (Intracranial Translucency) related to fetus, HC (Head Circumference), BPD (Bi-parietal Diameter), OFD (Occipital Frontal Diameter), Vp (Posterior Cerebral Ventricle Diameter), TCD (Transverse Cerebellar Diameter), CM (Cisterna Magna) related to a brain, and femur, tibia, fibula, ulna, radius, and humerus related to a bone.

22. An ultrasound diagnosis method comprising:
acquiring ultrasound data of a target object;
generating an ultrasound image by using the ultrasound data;
acquiring a standard view representing a plane of the target object including at least one of measurement objects used to diagnose the target object based on the ultrasound image, and information related to the standard view, the information comprising at least one among a type of the standard view, a location of the target object, and a direction of the target object;
setting a caliper to measure the target object on the standard view, based on a user input;
acquiring measurement information including caliper information of a position of the caliper and at least one point on the caliper, based on the standard view; and
automatically acquiring the at least one of the measurement objects being measured to diagnose the target object based on the caliper information indicating that the caliper is inclined from a predetermined line on the standard view by a value that is within a first range, and that the at least one point on the caliper is away from a predetermined point in the standard view by a value that is within a second range,
wherein the acquiring the at least one of the measurement objects comprises:
acquiring the measurement objects by determining whether the caliper is inclined by a value that is within the first range, or the at least one point on the caliper is away from the predetermined point by a value that is within the second range.

23. The ultrasound diagnosis method of claim 22, further comprising:
receiving user inputs on the acquired standard view; and
acquiring the measurement information based on the received user inputs.

24. A non-transitory computer-readable recording medium having recorded thereon a program which, when executed by a processor, causes the processor to execute the method of claim 22.

* * * * *